(12) United States Patent
Uddin et al.

(10) Patent No.: US 11,666,704 B2
(45) Date of Patent: Jun. 6, 2023

(54) ADMINISTRATION SYSTEM, DELIVERY DEVICE, AND NOTIFICATION DEVICE FOR COMMUNICATING STATUS OF A MEDICAL DEVICE

(71) Applicant: Becton, Dickinson and Company, Franklin Lakes, NJ (US)

(72) Inventors: Nasir Uddin, Secaucus, NJ (US); Mircea Despa, Cary, NC (US); Rekha Doshi Pursel, Londonderry, NH (US); John Richard Gyory, Sudbury, MA (US); Carlos Morales, Tewksbury, MA (US); Andrew Richards, Durham, NC (US); Matt Mooney, Westford, MA (US); Herve Abry, Champagnier (FR); Mark Bowen, Stow, MA (US); Rachel Zhang, Acton, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 3 days.

(21) Appl. No.: 16/038,626

(22) Filed: Jul. 18, 2018

(65) Prior Publication Data

US 2019/0022317 A1 Jan. 24, 2019

Related U.S. Application Data

(60) Provisional application No. 62/626,935, filed on Feb. 6, 2018, provisional application No. 62/559,051, filed on
(Continued)

(51) Int. Cl.
*A61M 5/20* (2006.01)
*A61M 5/142* (2006.01)
(Continued)

(52) U.S. Cl.
CPC ............. *A61M 5/20* (2013.01); *A61M 5/145* (2013.01); *A61M 5/148* (2013.01);
(Continued)

(58) Field of Classification Search
CPC .......... A61M 5/14244; A61M 5/14248; A61M 5/145; A61M 5/148; A61M 5/152;
(Continued)

(56) References Cited

U.S. PATENT DOCUMENTS

| 4,601,707 A | 7/1986 | Albisser et al. |
| 5,050,612 A | 9/1991 | Matsumura |

(Continued)

FOREIGN PATENT DOCUMENTS

| CN | 1218413 A | 6/1999 |
| CN | 1723053 A | 1/2006 |

(Continued)

*Primary Examiner* — Laura A Bouchelle
*Assistant Examiner* — John A Doubrava
(74) *Attorney, Agent, or Firm* — The Webb Law Firm

(57) ABSTRACT

An administration system for delivery of a pharmaceutical composition to a patient has a delivery device configured to deliver a dose of the pharmaceutical composition to the patient and a notification device in communication with the delivery device. The notification device is configured to communicate information about a status of at least one property of the delivery device. The delivery device can be a wearable automatic injector configured to be worn on the patient's skin. The delivery device of the present disclosure may allow a user or the patient to view a status of a container. For example, the delivery device of the present disclosure may provide a simple and effective visual means of displaying fill confirmation and delivery confirmation.

23 Claims, 18 Drawing Sheets

Related U.S. Application Data on Sep. 15, 2017, provisional application No. 62/533,954, filed on Jul. 18, 2017.

(51) Int. Cl.

| | | |
|---|---|---|
| *A61M 5/145* | (2006.01) | |
| *A61M 5/168* | (2006.01) | |
| *G16H 20/17* | (2018.01) | |
| *A61M 5/14* | (2006.01) | |
| *A61M 5/148* | (2006.01) | |
| *A61M 5/32* | (2006.01) | |
| *A61M 5/31* | (2006.01) | |

(52) U.S. Cl.
CPC ...... *A61M 5/1418* (2013.01); *A61M 5/14244* (2013.01); *A61M 5/14248* (2013.01); *A61M 5/16831* (2013.01); *A61M 5/3275* (2013.01); *G16H 20/17* (2018.01); *A61M 2005/14506* (2013.01); *A61M 2005/3125* (2013.01); *A61M 2205/3569* (2013.01); *A61M 2205/3584* (2013.01); *A61M 2205/58* (2013.01)

(58) Field of Classification Search
CPC .. A61M 2205/0216; A61M 2205/0227; A61M 2205/35; A61M 2205/3569; A61M 5/20; A61M 2005/14252
See application file for complete search history.

(56) References Cited

U.S. PATENT DOCUMENTS

| | | | |
|---|---|---|---|
| 5,135,479 A | 8/1992 | Sibalis et al. | |
| 5,318,540 A | 6/1994 | Athayde et al. | |
| 5,569,186 A | 10/1996 | Lord et al. | |
| 5,591,123 A | 1/1997 | Sibalis et al. | |
| 5,746,711 A | 5/1998 | Sibalis et al. | |
| 5,865,786 A | 2/1999 | Sibalis et al. | |
| 5,891,097 A * | 4/1999 | Saito | A61M 5/1483 604/141 |
| 5,925,021 A | 7/1999 | Castellano et al. | |
| 5,928,195 A | 7/1999 | Malamud et al. | |
| 5,950,632 A | 9/1999 | Reber et al. | |
| 6,238,338 B1 | 5/2001 | DeLuca et al. | |
| 6,248,090 B1 | 6/2001 | Jensen et al. | |
| 6,551,276 B1 | 4/2003 | Mann et al. | |
| 6,554,798 B1 | 4/2003 | Mann et al. | |
| 6,589,229 B1 | 7/2003 | Connelly et al. | |
| 6,699,234 B2 | 3/2004 | Yeh | |
| 6,749,587 B2 | 6/2004 | Flaherty | |
| 6,780,171 B2 | 8/2004 | Gabel et al. | |
| 6,872,200 B2 | 3/2005 | Mann et al. | |
| 6,997,920 B2 | 2/2006 | Mann et al. | |
| 7,109,878 B2 | 9/2006 | Mann et al. | |
| 7,133,329 B2 | 11/2006 | Skyggebjerg et al. | |
| 7,156,838 B2 | 1/2007 | Gabel et al. | |
| 7,282,029 B1 | 10/2007 | Poulsen et al. | |
| 7,397,730 B2 | 7/2008 | Skyggebjerg et al. | |
| 7,942,844 B2 | 5/2011 | Moberg et al. | |
| 8,073,008 B2 | 12/2011 | Mehta et al. | |
| 8,095,692 B2 | 1/2012 | Mehta et al. | |
| 8,102,796 B2 | 1/2012 | Kekalainen et al. | |
| 8,333,752 B2 | 12/2012 | Veit et al. | |
| 8,348,885 B2 | 1/2013 | Moberg et al. | |
| 8,487,758 B2 | 7/2013 | Istoc | |
| 8,506,523 B2 | 8/2013 | Miyazaki et al. | |
| 8,539,622 B2 | 9/2013 | West | |
| 8,568,361 B2 | 10/2013 | Yodat et al. | |
| 8,641,672 B2 | 2/2014 | Yodat et al. | |
| 8,663,201 B2 | 3/2014 | Hill et al. | |
| 8,679,062 B2 | 3/2014 | Yodat et al. | |
| 8,845,613 B2 | 9/2014 | Yodat et al. | |
| 8,888,744 B2 | 11/2014 | Yodat et al. | |
| 8,922,330 B2 * | 12/2014 | Moberg | G16H 40/63 340/3.1 |
| 8,992,475 B2 | 3/2015 | Mann et al. | |
| 8,995,237 B2 | 3/2015 | Vouillamoz | |
| 9,101,714 B2 | 8/2015 | Miyazaki et al. | |
| 9,107,586 B2 | 8/2015 | Tran | |
| 9,138,531 B2 | 9/2015 | Yodat et al. | |
| 9,211,377 B2 | 12/2015 | DiPerna et al. | |
| 9,248,231 B2 | 2/2016 | Yodat et al. | |
| 9,259,531 B2 | 2/2016 | Kamen et al. | |
| 9,415,157 B2 | 8/2016 | Mann et al. | |
| RE46,217 E | 11/2016 | Huang et al. | |
| 9,486,574 B2 | 11/2016 | Yodat et al. | |
| 10,258,735 B2 | 4/2019 | Edwards et al. | |
| 2002/0126036 A1 | 9/2002 | Flaherty et al. | |
| 2002/0133120 A1 | 9/2002 | Yeh | |
| 2003/0073952 A1 * | 4/2003 | Flaherty | A61M 5/14248 604/151 |
| 2003/0088238 A1 | 5/2003 | Poulsen et al. | |
| 2004/0116847 A1 | 6/2004 | Wall | |
| 2006/0122577 A1 | 6/2006 | Poulsen et al. | |
| 2007/0049865 A1 | 3/2007 | Radmer et al. | |
| 2007/0060869 A1 | 3/2007 | Tolle et al. | |
| 2007/0060870 A1 | 3/2007 | Tolle et al. | |
| 2007/0093786 A1 * | 4/2007 | Goldsmith | A61B 5/14532 604/890.1 |
| 2008/0004601 A1 | 1/2008 | Jennewine et al. | |
| 2008/0300572 A1 | 12/2008 | Rankers et al. | |
| 2008/0319414 A1 * | 12/2008 | Yodfat | A61B 5/6849 604/157 |
| 2009/0209938 A1 * | 8/2009 | Aalto-Setala | G16H 10/65 604/503 |
| 2009/0227855 A1 | 9/2009 | Hill et al. | |
| 2009/0240193 A1 | 9/2009 | Mensinger et al. | |
| 2010/0010330 A1 | 1/2010 | Rankers et al. | |
| 2011/0266999 A1 | 11/2011 | Yodat et al. | |
| 2012/0010594 A1 | 1/2012 | Holt et al. | |
| 2012/0091813 A1 | 4/2012 | Spurlin et al. | |
| 2012/0259185 A1 * | 10/2012 | Yodfat | A61M 5/14244 604/117 |
| 2014/0107607 A1 | 4/2014 | Estes | |
| 2014/0135699 A1 * | 5/2014 | Gyory | A61M 5/148 604/151 |
| 2014/0135700 A1 * | 5/2014 | Gyory | A61M 5/1483 604/151 |
| 2014/0194816 A1 | 7/2014 | Gray et al. | |
| 2014/0276587 A1 * | 9/2014 | Imran | A61M 5/148 604/506 |
| 2015/0207626 A1 | 7/2015 | Neftel et al. | |
| 2015/0209510 A1 | 7/2015 | Burkholz et al. | |
| 2016/0129182 A1 * | 5/2016 | Schuster | G16H 40/63 702/56 |
| 2016/0133345 A1 | 5/2016 | Vouillamoz | |
| 2016/0166766 A1 | 6/2016 | Schuster et al. | |
| 2016/0206808 A1 | 7/2016 | Gray et al. | |
| 2016/0206809 A1 | 7/2016 | Kamen et al. | |
| 2016/0256627 A1 | 9/2016 | Gray et al. | |
| 2016/0310663 A1 | 10/2016 | Dantsker | |
| 2016/0354553 A1 | 12/2016 | Anderson et al. | |
| 2016/0354562 A1 | 12/2016 | Morrison | |
| 2017/0042713 A1 | 2/2017 | Nurmikko et al. | |
| 2017/0043088 A1 | 2/2017 | Mann et al. | |
| 2017/0056578 A1 | 3/2017 | Kamen et al. | |
| 2017/0056584 A1 | 3/2017 | Kamen et al. | |
| 2017/0056585 A1 | 3/2017 | Kamen et al. | |
| 2017/0065765 A1 | 3/2017 | Gray | |
| 2017/0100536 A1 | 4/2017 | Estes | |
| 2017/0162277 A9 | 6/2017 | Vouillamoz | |
| 2017/0172522 A1 | 6/2017 | Insler et al. | |
| 2017/0173260 A1 | 6/2017 | Li et al. | |
| 2017/0173261 A1 | 6/2017 | O'Connor et al. | |
| 2017/0311816 A1 * | 11/2017 | Jeter | A61B 5/1123 |
| 2019/0099551 A1 * | 4/2019 | Yodfat | A61M 5/14244 |

FOREIGN PATENT DOCUMENTS

| | | | |
|---|---|---|---|
| CN | 101500624 A | 8/2009 | |
| CN | 103025369 A | 4/2013 | |
| CN | 205145297 U | 4/2016 | |
| EP | 1502613 A1 | 2/2005 | |

(56) References Cited

FOREIGN PATENT DOCUMENTS

| | | | |
|---|---|---|---|
| JP | 10192396 | A | 7/1998 |
| JP | 2012501771 | A | 1/2012 |
| JP | 2012508081 | A | 4/2012 |
| JP | 2015156902 | A | 9/2015 |
| JP | 2015531184 | A | 10/2015 |
| WO | 2013136802 | A1 | 9/2013 |
| WO | 2010029054 | A1 | 3/2020 |

* cited by examiner

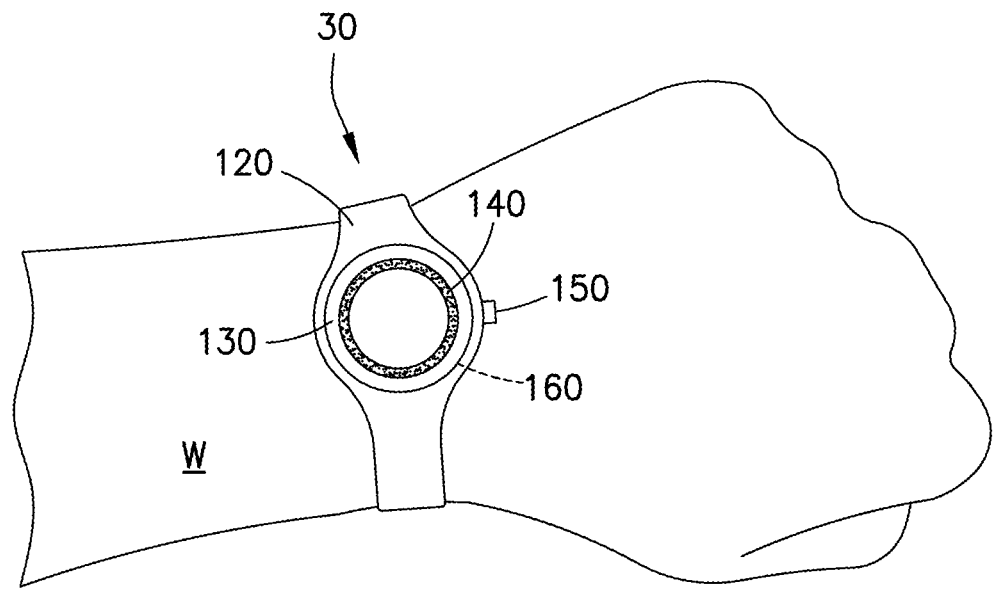
FIG.4
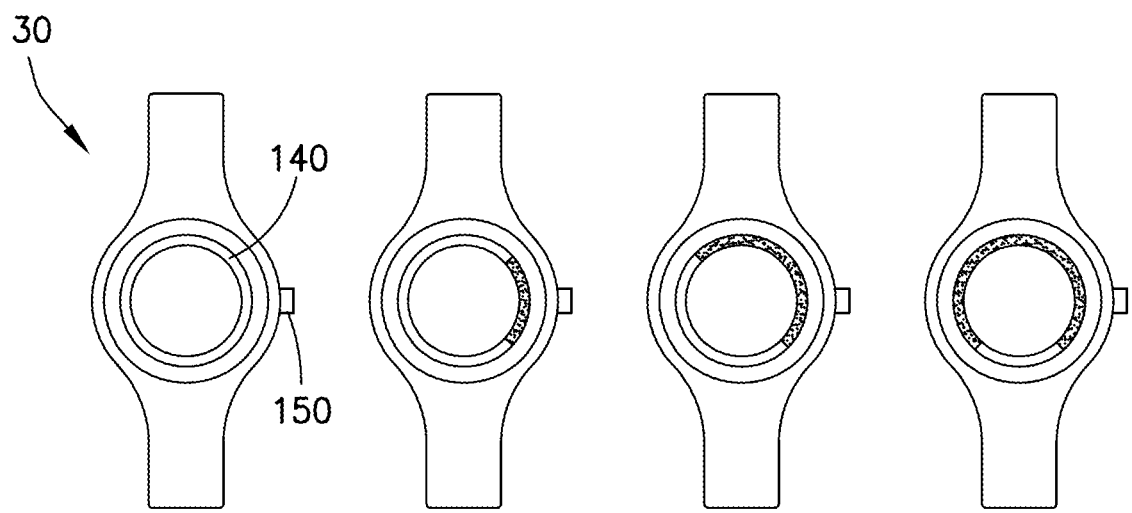
FIG.5A  FIG.5B  FIG.5C  FIG.5D

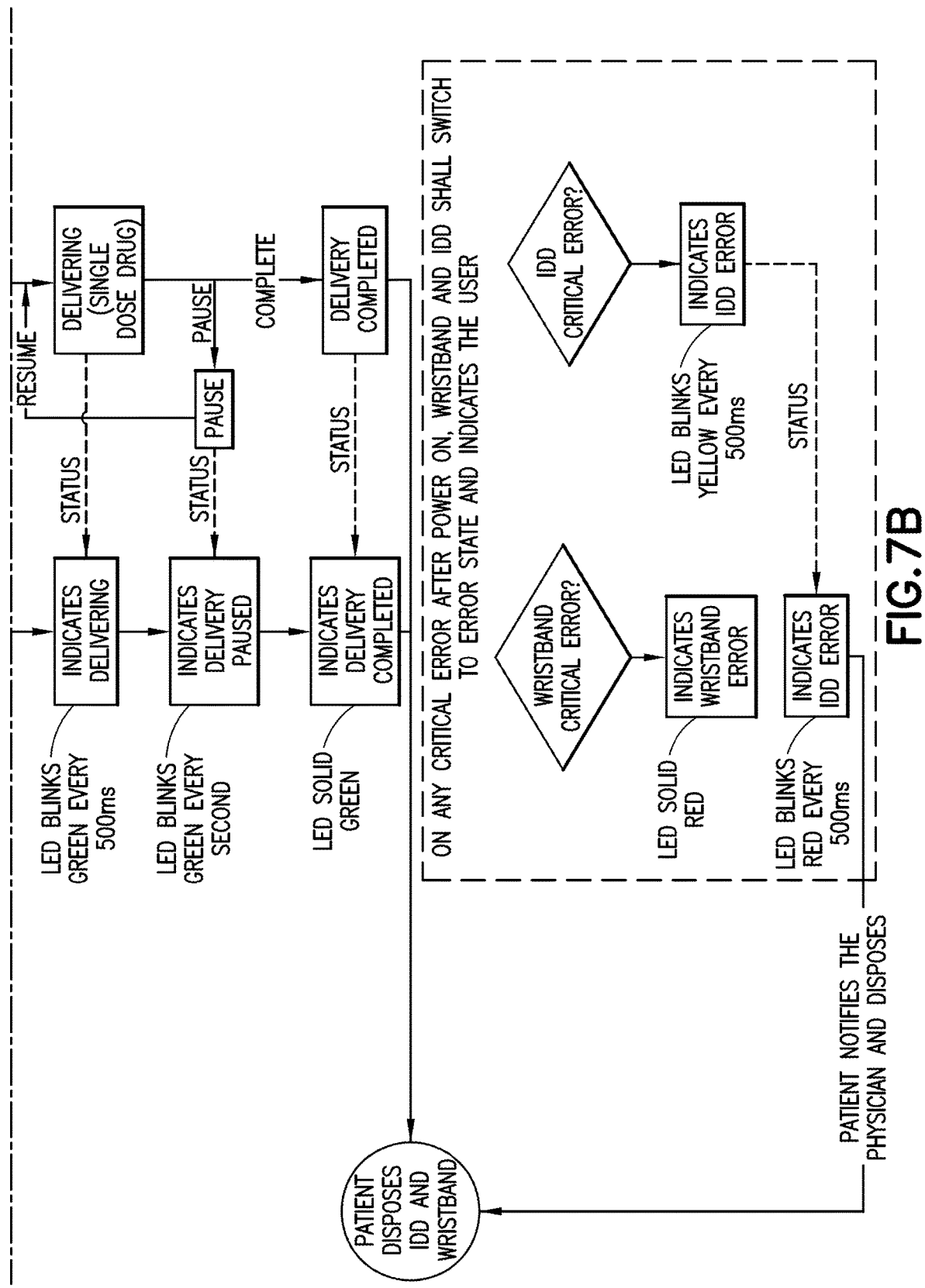

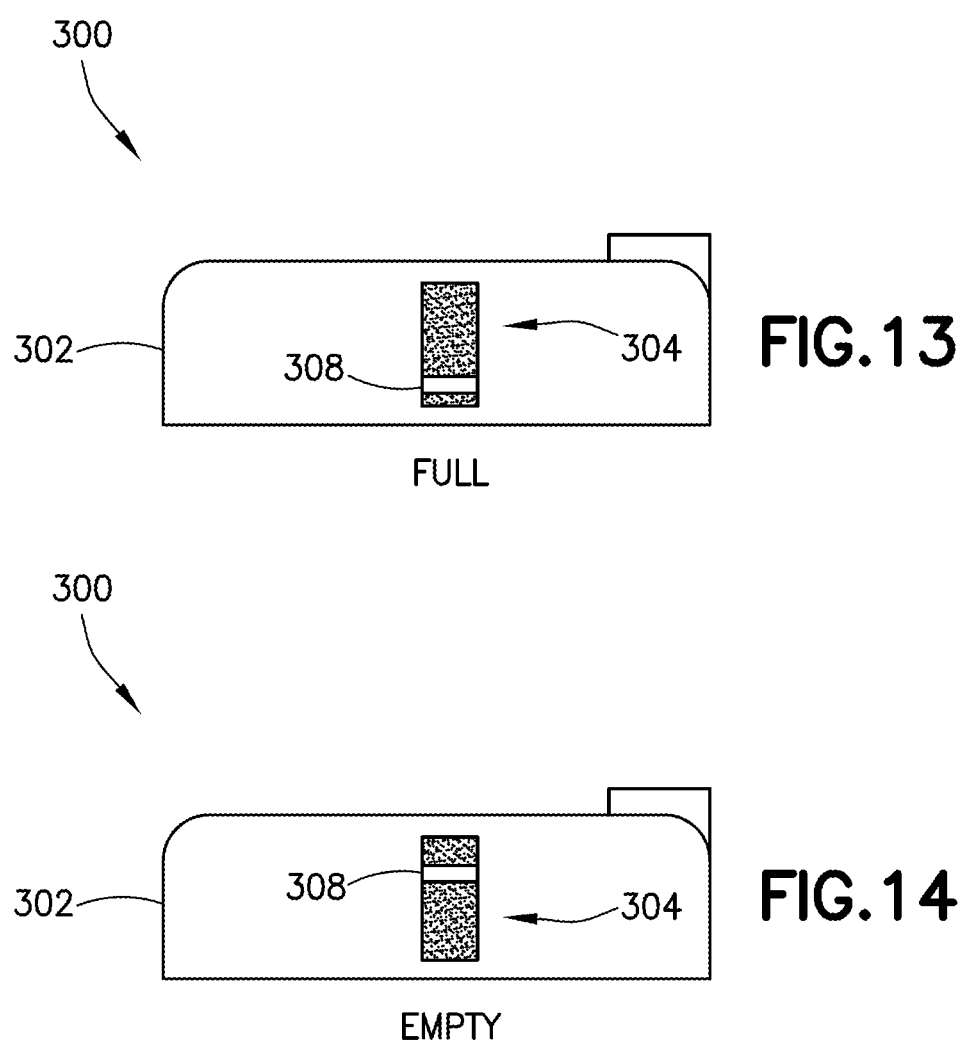

ADMINISTRATION SYSTEM, DELIVERY DEVICE, AND NOTIFICATION DEVICE FOR COMMUNICATING STATUS OF A MEDICAL DEVICE

CROSS-REFERENCE TO RELATED APPLICATIONS

The present application claims priority to U.S. Provisional Application Ser. No. 62/533,954 entitled "Notification Device for Communicating Status of a Medical Device" filed Jul. 18, 2017, the present application also claims priority to U.S. Provisional Application Ser. No. 62/559,051 entitled "Notification Device for Communicating Status of a Medical Device" filed Sep. 15, 2017, the present application also claims priority to U.S. Provisional Application Ser. No. 62/626,935 entitled "Administration System, Delivery Device, and Notification Device for Communicating Status of a Medical Device" filed Feb. 6, 2018, the entire disclosures of each of which are hereby incorporated by reference.

BACKGROUND OF THE INVENTION

Field of the Invention

The present disclosure relates generally to devices, systems, and methods for the delivery of pharmaceutical compositions to a patient. More particularly, the present disclosure relates to devices, systems, and methods for the delivery of pharmaceutical compositions to a patient using an automatic injector and to a notification device for communicating at least one property of the automatic injector, and to devices allowing a patient to view the status of a container such as a visual means of displaying fill confirmation and/or delivery confirmation.

Description of Related Art

Wearable medical devices, such as automatic injectors, have the benefit of providing therapy to the patient at a location remote from a clinical facility and/or while being worn discretely under the patient's clothing. On a physician's determination, the wearable medical device can be applied to the patient's skin and configured to automatically deliver a dose of the pharmaceutical composition within a predetermined time period after applying the wearable medical device to the patient's skin, such as after a 27 hour delay. After the device delivers the pharmaceutical composition to the patient, the patient may subsequently remove and dispose of the device.

Some wearable medical devices have the capability of communicating at least one property of the device to the patient. For example, some devices may provide a direct on-device visual, audible, or tactile feedback to the patient to inform the patient about the state of the device, such as when the device is delivering the pharmaceutical composition to the patient or when the delivery procedure is completed. While existing devices provide discreteness, one drawback of this is that any visual, audible, or tactile feedback of the device cannot be easily communicated to the patient because the device is obstructed by the patient's clothing or by the placement of the device on a particular location on the patient's body. For example, notifications issued by the device have limited visibility when the device is placed on the back of the patient's arm, often requiring a caregiver to observe the notifications. Additionally, in cases when the device is worn on the patient's abdomen, the device is obstructed by the patient's clothing and cannot be easily checked without removing the patient's clothing.

Accordingly, there is a need in the art for the delivery of pharmaceutical compositions to a patient using an automatic injector and to a notification device for communicating at least one property of the automatic injector.

SUMMARY OF THE INVENTION

The present disclosure provides for the device for the delivery of pharmaceutical compositions to a patient using an automatic injector and to a notification device for communicating at least one property of the automatic injector.

In some examples, an administration system for delivery of a pharmaceutical composition to a patient may have a delivery device configured to deliver a dose of the pharmaceutical composition to the patient and a notification device in communication with the delivery device. The notification device may be configured to communicate information about a status of at least one property of the delivery device. The delivery device may be a wearable automatic injector configured to be worn on the patient's skin. The notification device may have at least one indicator. The at least one indicator may be a visual indicator, an audible indicator, a tactile indicator, or a combination thereof. The notification device may be a wristband. The at least one property of the delivery device may include a delivery status of the delivery device.

In accordance with an embodiment of the present invention, a delivery apparatus is configured to deliver a dose of a medicament to a patient. The delivery system includes a delivery device having a housing including a viewing window, a flexible container disposed within the housing and for storing the medicament therein, and a visual identifier aligned with a portion of the viewing window, wherein a position of the visual identifier relative to the viewing window is dependent on a volume of the medicament within the container. The delivery apparatus also includes a notification device in communication with the delivery device, the notification device configured to communicate information about a status of at least one property of the delivery device.

In another configuration, the visual identifier is movable relative to the viewing window between an empty position, in which the container is empty, and a full position, in which the container is full. The visual identifier may include a connector that is attachable to a portion of the container. The connector may be attachable to a sealed edge of the container, and the connector may include an indicator clip.

The visual identifier may be disposed within the housing between the container and a deformable material. As the container is filled with the medicament, the container expands and moves the visual identifier downward thereby compressing the deformable material. As the container delivers the medicament, the container shrinks and the deformable material expands thereby moving the visual identifier upward. Optionally, the deformable material comprises a foam.

In certain configurations, the visual identifier includes a deflectable member. As the container is filled with the medicament, the container expands and deflects one end of the deflectable member downward. As the container delivers the medicament, the container shrinks and the one end of the deflectable member returns to its original position. The housing may include a fill-indicator display adjacent the viewing window. The visual identifier may align with a portion of the fill-indicator display to identify an amount of medicament within the container. The container may be a reservoir bag and the visual identifier may be a portion of the reservoir bag.

In certain configurations, the viewing window is located in a sidewall of the housing. The delivery device may be a wearable automatic injector removably attachable to a skin surface of the patient. Optionally, the delivery device includes at least one indicator for communicating a condition of the delivery device to the patient. The notification device may be a wristband, and the notification device may be in passive one-way communication with the delivery device and wherein the notification device displays a status of at least one property of the delivery device.

In accordance with another embodiment of the present invention, an administration system for delivery of a pharmaceutical composition to a patient includes a delivery device configured to deliver a dose of the pharmaceutical composition to the patient, and a notification device in communication with the delivery device, the notification device configured to communicate information about a status of at least one property of the delivery device. The notification device is in passive one-way communication with the delivery device, and the notification device displays a status of at least one property of the delivery device.

In certain configurations, the delivery device is a wearable automatic injector configured to be worn on the patient's skin. The notification device may include at least one indicator. The at least one indicator may be a visual indicator, an audible indicator, a tactile indicator, or a combination thereof. Optionally, the notification device is a wristband and the at least one property of the delivery device comprises a delivery status of the delivery device. The delivery device may include a reservoir bag configured to contain a medicament therein and the reservoir bag may include a visual identifier. The delivery device may further include a fill-indicator display, and the visual identifier of the reservoir bag is configured to align with a portion of the fill-indicator display depending on the volume of medicament disposed within the reservoir bag. Optionally, the delivery device further includes at least one indicator capable of communicating a condition of the delivery device to a user, wherein the indicator may be an LED.

These and other features and characteristics of an administration system and methods of using the same will become more apparent upon consideration of the following description and the appended claims with reference to the accompanying drawings, all of which form a part of this specification, wherein like reference numerals designate corresponding parts in the various drawings. It is to be expressly understood, however, that the drawings are for the purpose of illustration and description only.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 4 is a perspective view of a notification device for use with a wearable automatic injector in accordance with an embodiment of the present invention;

FIG. 5A is a top view of a display of a notification device for use with a wearable automatic injector showing an initial pre-use state in accordance with an embodiment of the present invention;

FIG. 5B is a top view of a display of a notification device for use with a wearable automatic injector showing a state of indication after a first period of time has elapsed after initiation in accordance with an embodiment of the present invention;

FIG. 5C is a top view of a display of a notification device for use with a wearable automatic injector showing a state of indication after a second period of time has elapsed after initiation in accordance with an embodiment of the present invention;

FIG. 5D is a top view of a display of a notification device for use with a wearable automatic injector showing a state of indication after a third period of time has elapsed after initiation in accordance with an embodiment of the present invention;

FIGS. 7A-7B are schematic representations of a life cycle of a wearable automatic injector and notification device in accordance with an embodiment of the present invention;

FIG. 13 is a side view of a wearable automatic injector having a viewing window with a visual identifier aligned within the viewing window in a full position in accordance with an embodiment of the present invention;

FIG. 14 is a side view of a wearable automatic injector having a viewing window with a visual identifier aligned within the viewing window in an empty position in accordance with an embodiment of the present invention;

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION OF THE INVENTION

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". By "about" is meant a range of plus or minus ten percent of the stated value. As used in the specification and the claims, the singular form of "a", "an", and "the" include plural referents unless the context clearly dictates otherwise.

The terms "first", "second", and the like are not intended to refer to any particular order or chronology, but instead refer to different conditions, properties, or elements. By "at least" is meant "greater than or equal to". By "not greater than" is meant "less than or equal to".

Administration System

Figure 1:
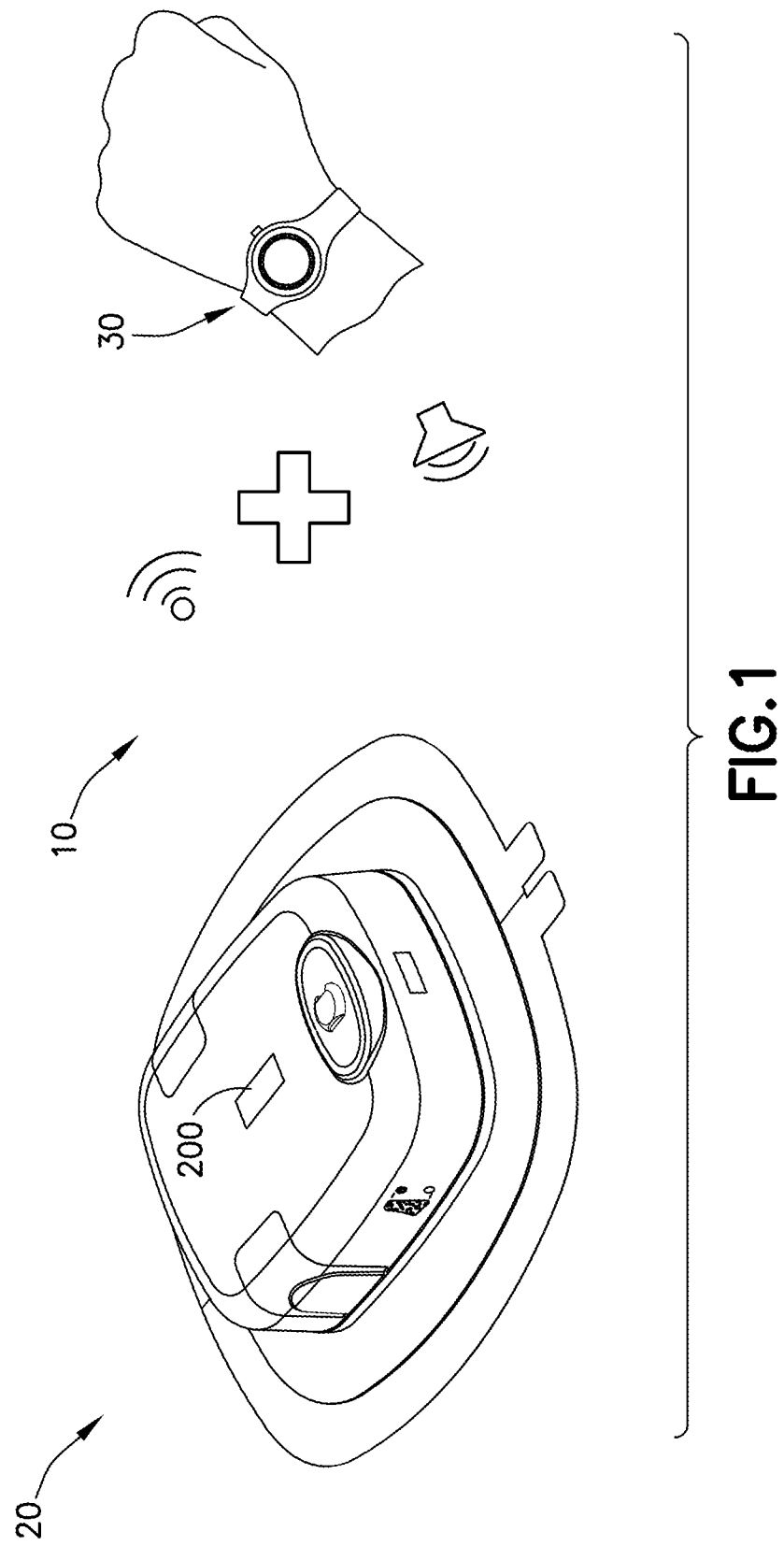
FIG. 1 is a perspective view of a wearable automatic injector and a notification device paired to the wearable automatic injector in accordance with an embodiment of the present invention.

With reference to FIG. 1, an administration system 10 for delivery of a pharmaceutical composition, e.g., any desired medicament or therapeutic agent, to a patient may have a delivery device 20, such as a wearable automatic injector, configured to deliver a dose of the pharmaceutical composition to the patient and a notification device 30 in communication with the delivery device 20. The notification device 30 may be configured to communicate information about a status of at least one property of the delivery device 20.

In some examples, the notification device 30 may be in wireless electronic communication with the delivery device 20. In other examples, the notification device 30 may be in wired electronic communication with the delivery device 20. In some examples where the notification device 30 and the delivery device 20 are wirelessly connected, the notification device 30 may be configured for passive one-way communication with the delivery device 20 wherein the notification device 30 is configured to communicate information about a status of at least one property of the delivery device 20 without controlling any aspect of the delivery device 20. In other examples where the notification device 30 and the delivery device 20 are wirelessly connected, the notification device 30 may be configured for two-way communication with the delivery device 20 wherein the notification device 30 is configured to communicate information about a status of at least one property of the delivery device 20 and to control at least one aspect of the delivery device 20, such as activation, reset functions, and the like.

The notification device 30 may have at least one indicator. The at least one indicator may be a visual indicator, an audible indicator, a tactile indicator, or a combination thereof. The delivery device 20 and/or the notification device 30 may be disposable after a dose of the pharmaceutical composition is delivered to the patient. In some examples, the delivery device 20 may be disposable after a dose of the pharmaceutical composition is delivered to the patient, while the notification device 30 may be reusable with another delivery device 20.

Delivery Device

Figure 2:
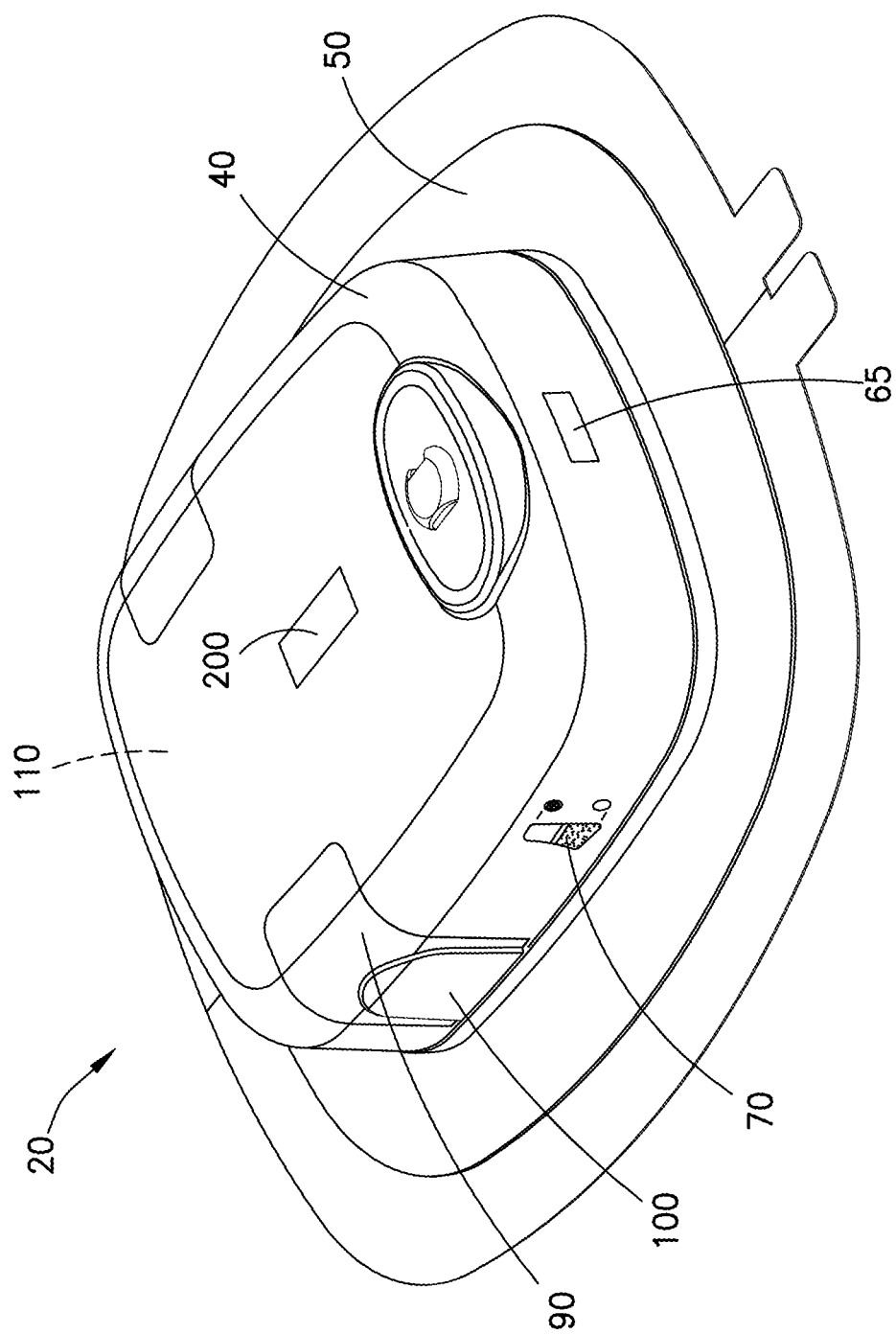
FIG. 2 is a perspective top view of a wearable automatic injector in accordance with an embodiment of the present invention.
Figure 3:
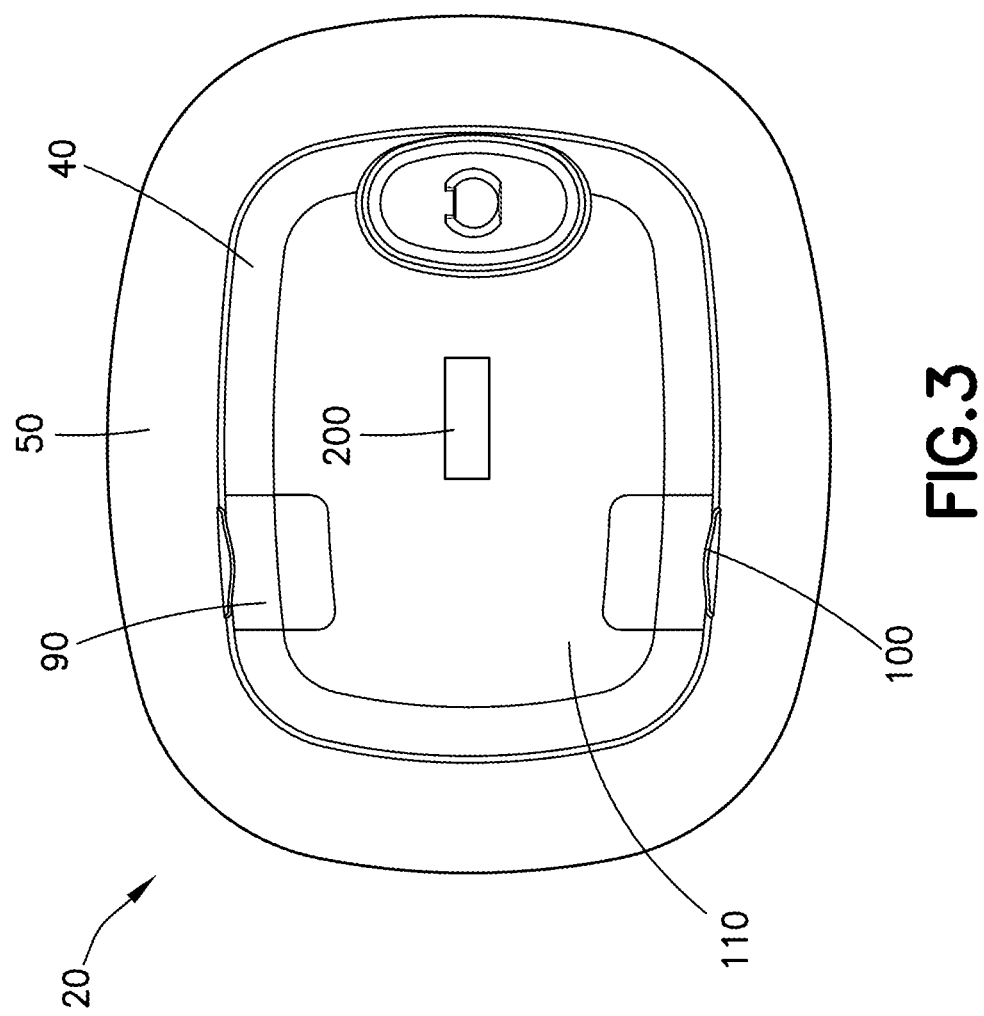
FIG. 3 is a top view of a wearable automatic injector in accordance with an embodiment of the present invention.

With reference to FIGS. 2-3, the delivery device 20 may be, in some examples, a wearable automatic injector, such as an insulin or bone marrow stimulant delivery device. In use, the delivery device 20 containing a pharmaceutical composition, e.g., any desired medicament, is mounted onto the skin of a patient and triggered to inject the pharmaceutical composition into the patient. The delivery device 20 may be pre-filled with the pharmaceutical composition, or it may be filled with the pharmaceutical composition by the patient or medical professional prior to use.

The delivery device 20 is configured to deliver a dose of a pharmaceutical composition, e.g., any desired medicament, into the patient's body by a subcutaneous injection at a slow, controlled injection rate. Exemplary time durations for the delivery achieved by the delivery device 20 may range from about 5 minutes to about 60 minutes, but are not limited to this exemplary range. Exemplary volumes of the pharmaceutical composition delivered by the delivery device 20 may range from about 0.1 milliliters to about 10 milliliters, but are not limited to this exemplary range. The volume of the pharmaceutical composition delivered to the patient may be adjusted.

With continued reference to FIGS. 2-3, the delivery device 20 has a housing 40 comprising a dermal pad 50 securable to the patient's skin. The dermal pad 50 may have an adhesive for adhesively connecting the delivery device 20 to the patient's skin. The housing 40 has an injection assembly (not shown) moveably disposed in the housing 40. The injection assembly has a hypodermic injection needle 60 (shown in FIG. 6B) for insertion into the patient. The injection assembly is configured for moving the injection needle 60 between a retracted position, in which the injection needle 60 does not protrude outside the housing 40, and an extended position, in which the injection needle 60 protrudes outside the housing 40 and through the dermal pad 50 such that the injection needle 60 can be inserted into the patient's body. The injection needle 60 may be retractable from the extended position to the retracted position after the pharmaceutical composition is delivered to the patient and prior to removal of the delivery device 20 from the patient's body. A window 65, or other indicator, may be provided on the housing 40 for visualizing the injection needle 60.

With continued reference to FIGS. 2-3, the delivery device 20 has an internal medicament container, such as a reservoir bag 306 (shown in FIG. 15) provided in the housing 40 for holding a volume of the medicament or therapeutic agent. The medicament or therapeutic agent may be delivered from the container through the injection needle 60 by a delivery mechanism of the injection assembly.

The delivery device 20 of the present disclosure allows a user or patient to view the status of the internal medicament container 306. For example, a delivery device of the present disclosure provides a simple and effective visual means of displaying fill confirmation and/or delivery confirmation. Referring to FIGS. 13-23, in exemplary embodiments, a delivery device 300 of the present disclosure is configured to deliver a dose of a medicament to a patient or user. The delivery device 300 generally includes a housing 302 including a viewing window 304, a medicament container 306, such as a reservoir bag, disposed within the housing 302 and for storing the medicament or therapeutic agent therein, and a visual identifier 308 aligned with a portion of the viewing window 304, wherein a position of the visual identifier 308 relative to the viewing window 304 is dependent on a volume of the medicament within the container 306.

In this manner, a user of the delivery device is able to easily view the status of a container 306. For example, a technician is able to easily determine if any medicament is stored within the container 306, how much medicament is stored within the container 306, if the container 306 is empty and needs to be filled with a medicament, and/or if the container 306 is full of a medicament and ready to be used by a patient, or if the medicament has been fully delivered from the container 306 into the patient.

Referring to FIGS. 10A-10C and FIGS. 15-21, in one embodiment, a container 306 includes at least one expandable portion 290 which is at least partially visible through a viewing window 280 disposed in at least a portion of the housing of the delivery device 20. In certain configurations, the entire container 306 may be expandable. For example, the container 306 may be made from a flexible material which expands in size as a fluid medicament is filled into the container 306. Optionally, the container 306 may have a visual indicator integrally formed therewith. In one embodiment, the container 306 may be made of a material having a visually distinct color, such as a fluorescent green material, such that the positioning of the container 306 within the viewing window 280 is readily identifiable. In this manner, when the container 306 is empty, a color band of the reservoir bag 290 being shown through the viewing window 280 appears to be a straight or near straight line located adjacent an empty indicator line. Also, as the container 306 is filled and expands, the width of the container 306 is increased thereby a color band of the container 306 being shown through the viewing window 280 appears to be a broad, wide band that expands to a point adjacent a full indicator line. In other configurations, the color band of the reservoir bag 290 may be provided in a first position within the viewing window 280 in an empty position, and may be provided in a second position within the viewing window 280 in a full position.

In other configurations, a visual identifier may be stamped or painted onto at least a portion of the container 306. The visual identifier may be in the form of a line or other distinct patterning, alternatively, the entire container 306 may include the visual identifier, such as an overall color of the container 306.

In one embodiment, a color band may be added to the container 306 by pad printing, roll printing, adhesive patch attachment, or other similar process. In one embodiment, a window may be added to a top cover of the delivery device 20 to allow visual sight to a colored edge of the container 306. In one embodiment, this is done by over printing or over labeling onto a clear top cover obscuring some regions of the top cover and allowing see through windows in other regions of the cover, multi-shot molding to create clear and opaque regions in the top cover, molding an opaque cover with a hole where the window is desired and incorporating a clear window part as a post processing step. It is also envisioned to create an opaque top cover without a window and through post processing steps cut a hole where the window is desired and then a window may be added to that location.

In one embodiment, the container 306 may be made of a material having a visually distinct color. For example, particular colors may be more advantageous and increase the viewability of the state and/or condition of the container 306. Also, the addition of lighting inside or outside of the system can be used to increase viewability. The window area may be reticulated to aid in the distinction between filled and unfilled states of the container 306.

In one embodiment, the entire container 306, or significant portions of the container 306, may be made of a material having a visually distinct color, such as a fluorescent green material, such that the positioning of the container 306, such as a reservoir bag, within the viewing window 280 is readily identifiable. In other configurations, a visual identifier 308 may be stamped or painted onto at least a portion of the container 306. The visual identifier 308 may be in the form of a line or other distinct patterning, alternatively, the entire container 306 may include the visual identifier 308, such as an overall color of the container 306. Depending on the particular nature of the medicament to be provided into the container 306, it may be desirable to provide a container 306 that is light-impermeable.

Figure 15:
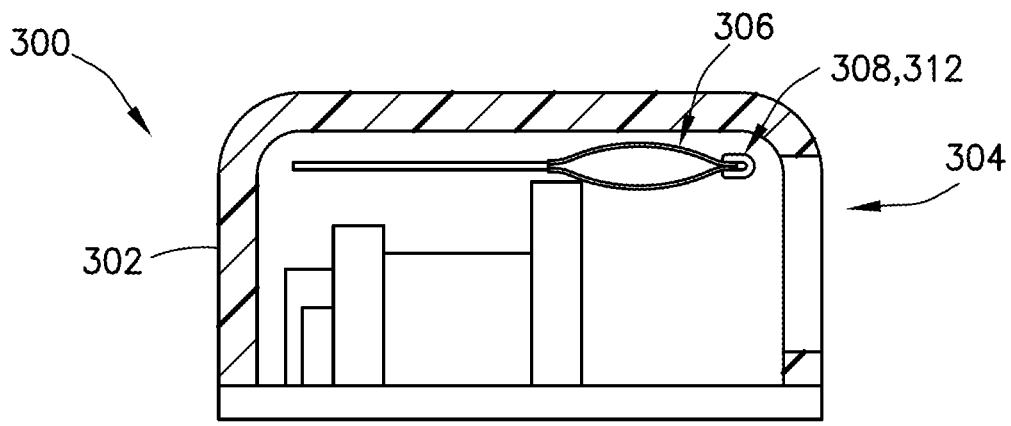
FIG. 15 is a cross-sectional front view of a wearable automatic injector housing with a visual identifier connector that is attachable to a portion of a medicament container, with the visual identifier in an empty position and aligned within the viewing window, in accordance with an embodiment of the present invention.
Figure 17:
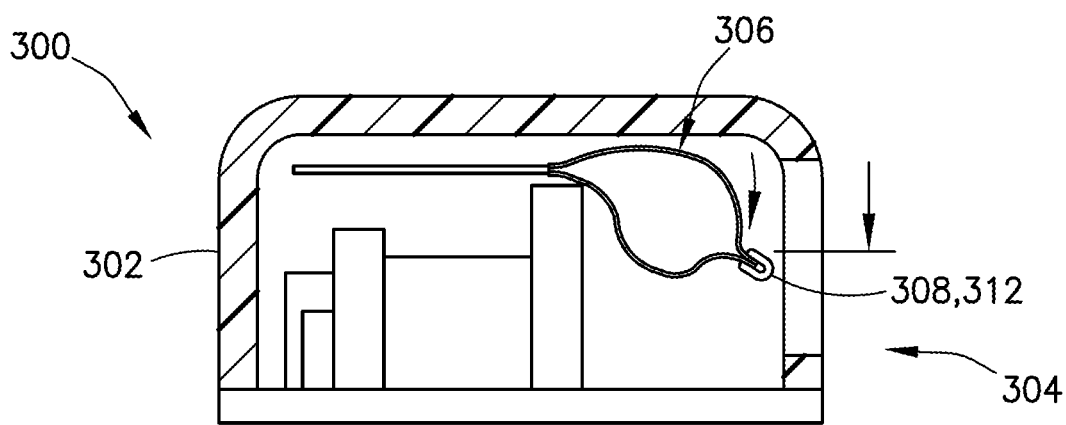
FIG. 17 is a cross-sectional front view of a wearable automatic injector housing with a visual identifier connector that is attachable to a portion of a medicament container, with the visual identifier in a filled position and aligned within the viewing window, in accordance with an embodiment of the present invention.

Referring to FIGS. 13 and 14, a separate visual identifier 308 of the present disclosure is movable relative to the viewing window 304 of a housing 302 of a delivery device 300 between an empty position (FIG. 14), in which the container 306 is empty, and a full position (FIG. 13), in which the container 306 is full. Referring to FIGS. 13 and 14, in one embodiment, as the container 306 is filled, the container 306 expands. In one embodiment, because the top of the container 306 is constrained by the top of the housing 302, e.g., as shown in FIGS. 15 and 17, the container 306 is forced to expand downward as it is filled. As the container 306 is forced in a downward direction, the separate visual identifier 308 may also be forced in a downward direction by the weight of the container 306 to transition the visual identifier 308 from a first position to a second position, indicative of the amount of medicament within the container 306. It is noted herein that the positioning of the visual identifier 308 may transition during both filling and also during delivery of the medicament. In this configuration, as the weight of the container 306 lessens as the contents of the container 306 are delivered to a patient, the visual identifier 308 may transition from a first position to a second position in an upward direction.

Referring to FIGS. 13 and 14, in one embodiment, the viewing window 304 is located in a sidewall of the housing 302. Referring to FIG. 3, in other embodiments, a viewing window 200 may be located in a top wall of a housing 40 of a delivery device 20. In other alternative embodiments, the viewing window of the present disclosure may be configured in other orientations to allow a user or patient to view the status of a container. The fill indicator 70 may have accompanying indicia indicating a volume of the pharmaceutical composition in the container. In some examples, the delivery device 20 may have a plurality of containers, with each container receiving the same or different pharmaceutical composition.

Figure 10A:
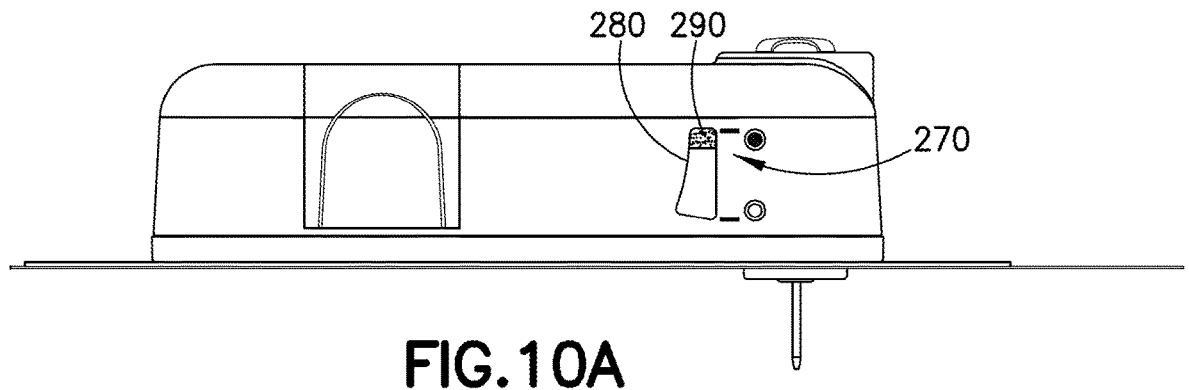
FIG. 10A is a schematic side view of a wearable automatic injector having a fill-indicator display in the prior to filling/empty condition in accordance with an embodiment of the present invention, the delivery needle is shown in an extended position for representation of the device only, and it is intended that the device may not include an extended delivery needle during the filling process.
Figure 10B:
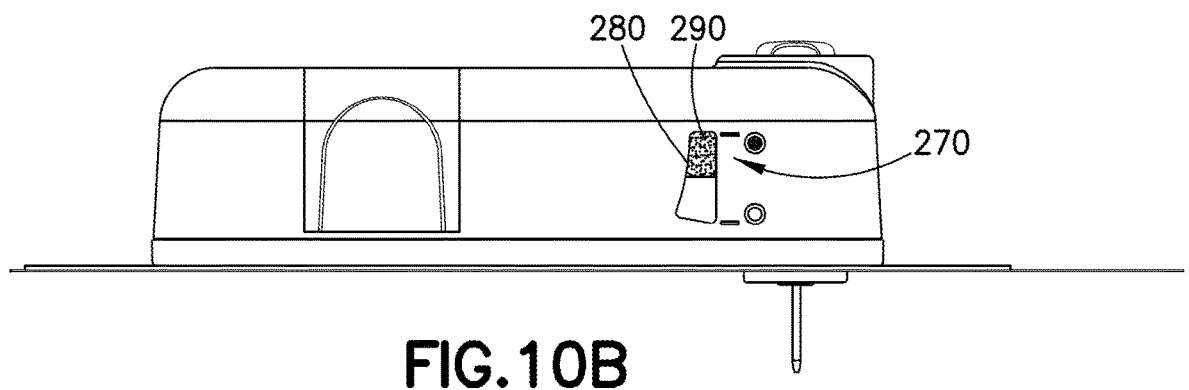
FIG. 10B is a schematic side view of a wearable automatic injector having a fill-indicator display in the partially filled/delivered condition in accordance with an embodiment of the present invention, the delivery needle is shown in an extended position for representation of the device only, and it is intended that the device may not include an extended delivery needle during the filling process.
Figure 10C:
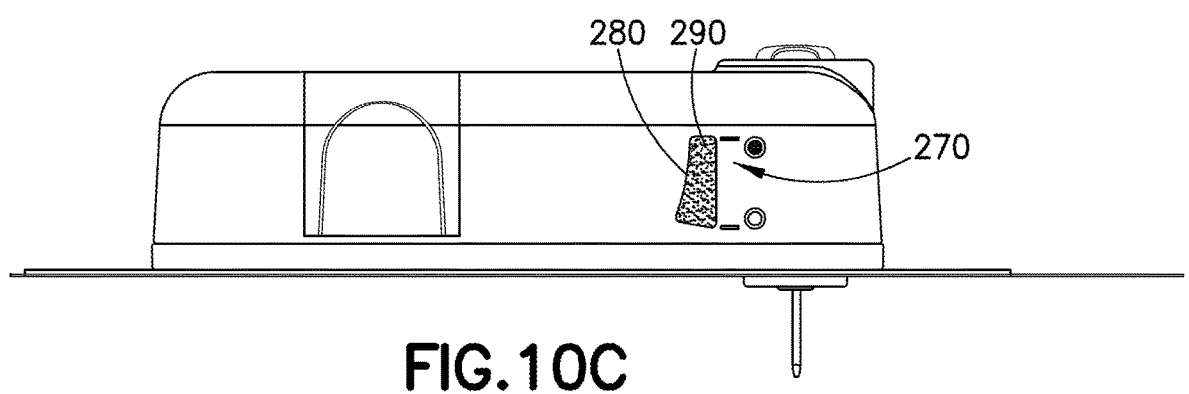
FIG. 10C is a schematic side view of a wearable automatic injector having a fill-indicator display in the filled condition in accordance with an embodiment of the present invention, the delivery needle is shown in an extended position for representation of the device only, and it is intended that the device may not include an extended delivery needle during the filling process.
Figure 11:
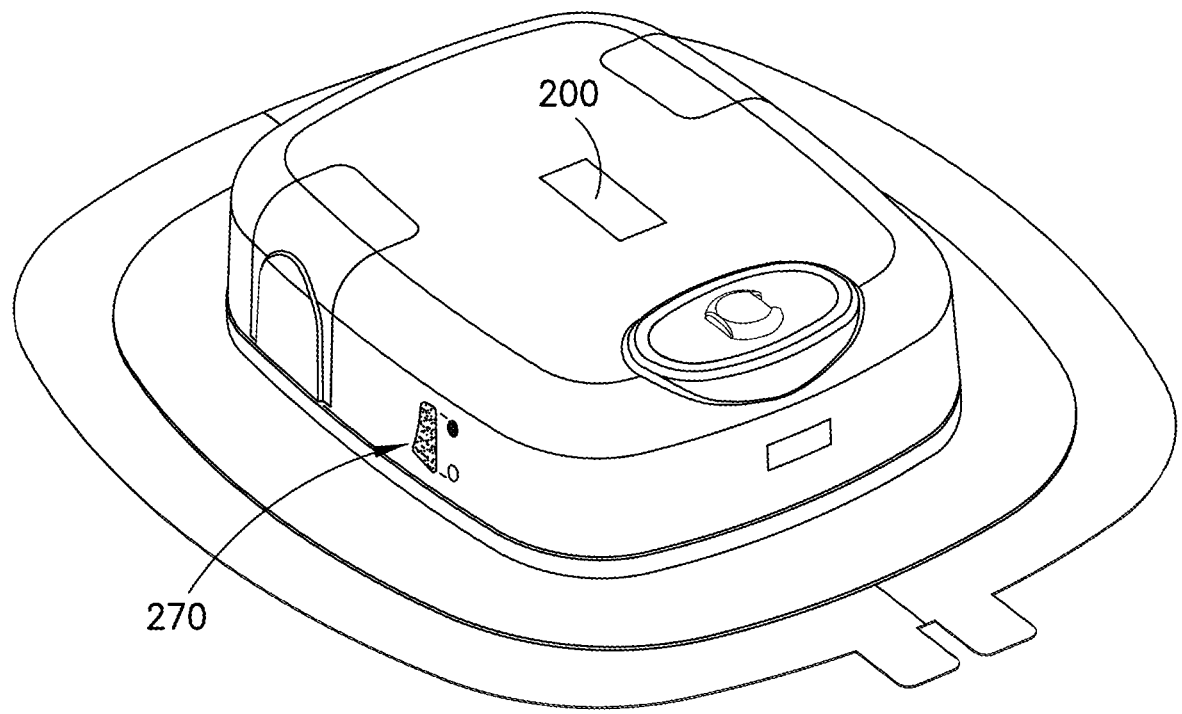
FIGS. 11-12 are perspective views of a wearable automatic injector having a fill-indicator display and a separate LED indicator in accordance with an embodiment of the present invention.

Referring to FIGS. 10A-11, in another exemplary embodiment, the delivery device 20 may have a viewing window or fill-indicator display 270 which includes a fill-line display indicating the prior to filling/empty condition, the partially filled/delivered condition, and the filled condition. In this manner, a technician can readily identify how much, if any, medicament is provided within the container 306. In this configuration, indicia on the housing of the delivery device 20 may align with the visual identifier of the container to indicate to a user and/or patient the amount of medicament within the container 306 at a given time.

Figure 16:
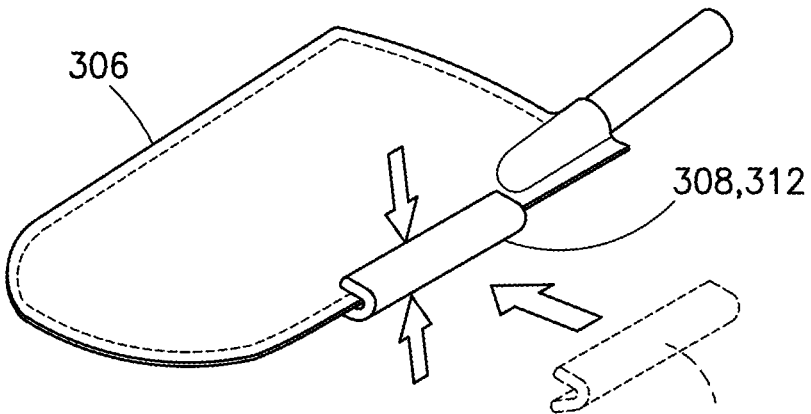
FIG. 16 is a perspective view of a medicament container for receipt within a wearable automatic injector, the medicament container having a visual identifier attachable thereto in accordance with an embodiment of the present invention.

Referring to FIGS. 15-17, in another exemplary embodiment, a connector 312 includes the visual identifier 308, with the connector 312 being attachable to a portion of the container 306. In one embodiment, the connector 312 is attachable to a sealed edge of the container 306. The connector 312 may include an indicator clip which can be secured to a portion of the container 306, such as along a container seam. The connector 312 may be movable relative to the viewing window 304 of a housing 302 of a delivery device 300 between an empty position (FIG. 15), in which the container 306 is empty, and a full position (FIG. 17), in which the container 306 is full. Movement within the viewing window 304 indicates to a user the content volume of the container 306.

Referring again to FIGS. 15 and 17, in one embodiment, as the container 306 is filled, it expands. In one embodiment, because the top of the container 306 is constrained by the top of the housing 302, the container 306 is forced to expand downward as it is filled. As the container 306 is filled, the connector 312 moves downward, and its movement is visible in the viewing window 304 of the housing 302.

Figure 18:
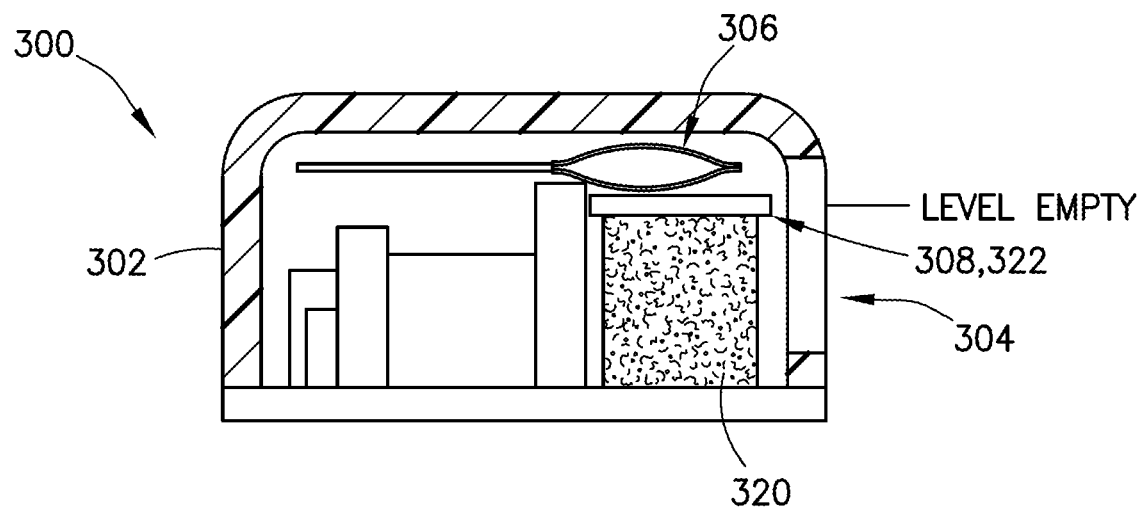
FIG. 18 is a cross-sectional front view of a wearable automatic injector housing with a visual identifier and a deformable material, with the visual identifier in an empty position, in accordance with an embodiment of the present invention.
Figure 19:
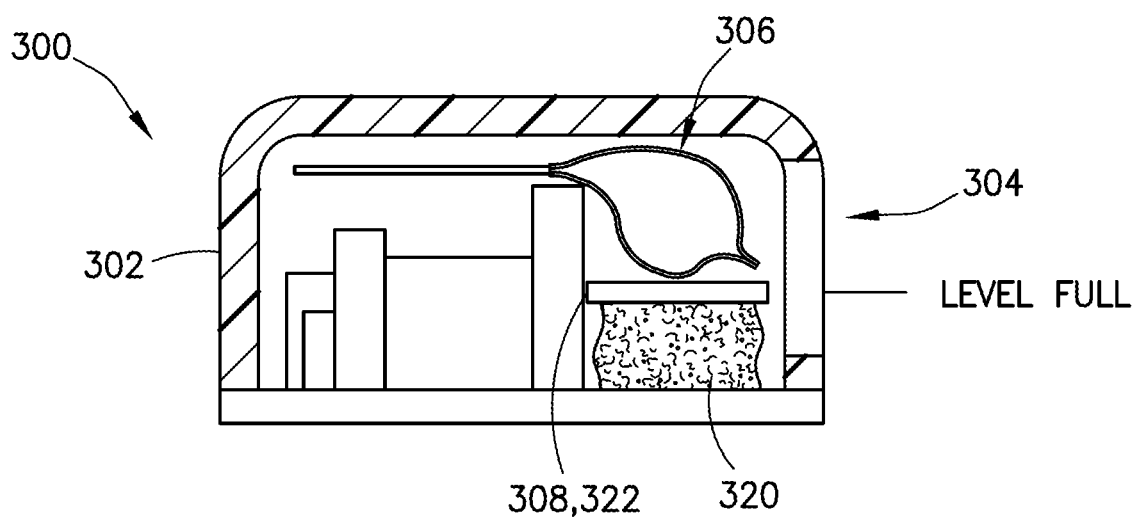
FIG. 19 is a cross-sectional front view of a wearable automatic injector housing with a visual identifier and a deformable material, with the visual identifier in a filled position and the deformable material in a compressed position, in accordance with an embodiment of the present invention.

Referring to FIGS. 18-19, in another exemplary embodiment, a visual identifier 308 is disposed within the housing 302 between the container 306 and a deformable material 320. The deformable material 320 serves to support the container 306 and to provide a consistent initial position, original state, or empty position, for the visual identifier 308, as shown in FIG. 18.

In one embodiment, the deformable material is a foam, such as a low density foam. As the container 306 is filled with medicament, the weight of the container 306 compresses the deformable material 320. A visual identifier 308 in the form of a rigid component 322, such as a plastic stiffener, may be disposed within the housing 302 between the container 306 and the deformable material 320 such that the visual identifier 308 is viewable through a portion of the viewing window 304, such as during filling of the container 306 to allow for visualization of the volume of content within the container 306 through the viewing window 304. The rigid component 322 is movable relative to the viewing window 304 of a housing 302 of a delivery device 300 between an empty position (FIG. 18), in which the container 306 is empty, and a full position (FIG. 19), in which the container 306 is full. As the container 306 is filled, the container 306 expands. In one embodiment, because the top of the container 306 is constrained by the top of the housing 302, e.g., as shown in FIGS. 18 and 19, the container 306 is forced to expand downward as it is filled. As the container 306 is filled, the rigid component 322 moves downward, and its movement is visible in the viewing window 304 of the housing 302. As the container 306 delivers the medicament, the container 306 shrinks and the deformable material 320 expands thereby moving the rigid component 322 upward. With the rigid component 322 in the empty position (FIG. 18), the deformable material 320 is in an original state, and with the rigid component 322 in the full position (FIG. 19), the deformable material 320 is compressed.

Figure 20:
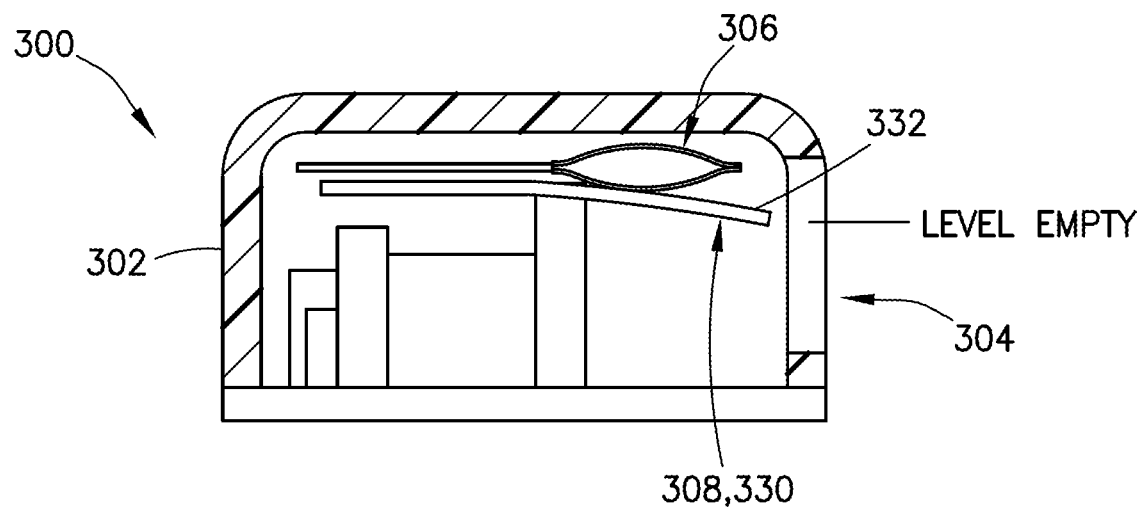
FIG. 20 is a cross-sectional front view of a wearable automatic injector housing with a visual identifier including a deflectable member, with the visual identifier in an empty position, in accordance with an embodiment of the present invention.
Figure 21:
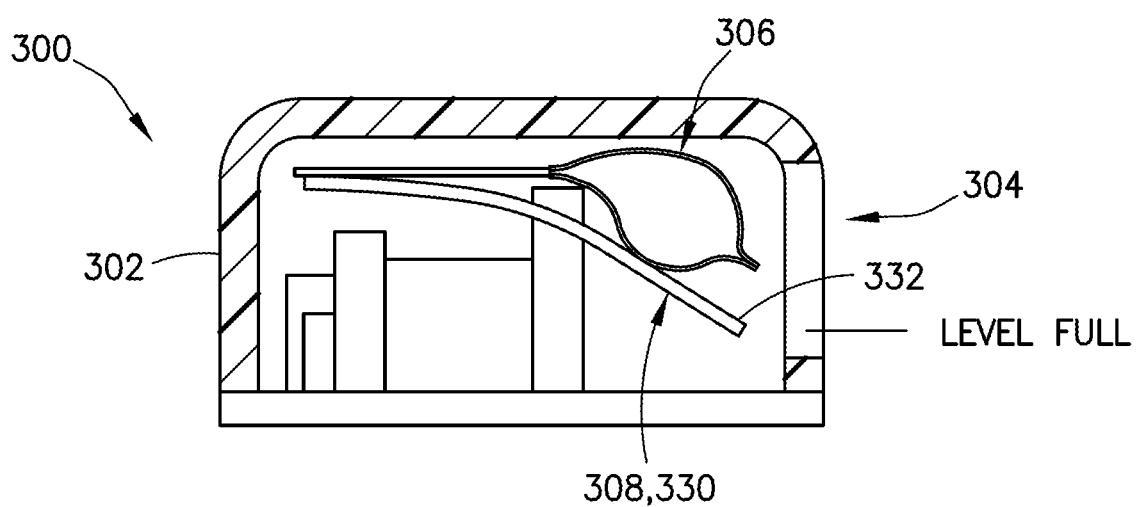
FIG. 21 is a cross-sectional front view of a wearable automatic injector housing with a visual identifier including a deflectable member, with the visual identifier in a filled position, in accordance with an embodiment of the present invention.

Referring to FIGS. 20-23, in another exemplary embodiment, a visual identifier 308 includes a deflectable member 330. In one embodiment, the visual identifier 308 is a flexible cantilever such as a long stiffener. In one embodiment, a deflectable member 330 allows for a greater range of movement of the visual identifier 308 relative to the viewing window 304 of the housing 302 of the delivery device 300. Referring to FIGS. 20 and 21, a deflectable member 330 of the present disclosure is movable relative to the viewing window 304 of a housing 302 of a delivery device 300 between an empty position (FIG. 20), in which the container 306 is empty, and a full position (FIG. 21), in which the container 306 is full. As the container 306 is filled, the container 306 expands. In one embodiment, because the top of the container 306 is constrained by the top of the housing 302, e.g., as shown in FIGS. 20 and 21, the container 306 is forced to expand downward as it is filled. As the container 306 is filled, the deflectable member 330 moves downward, and its movement is visible in the viewing window 304 of the housing 302. As the container 306 is filled with the medicament, the container 306 expands and deflects one end, e.g., a first end 332, of the deflectable member 330 downward. In one embodiment, as the container 306 delivers the medicament, the container 306 shrinks and the one end, e.g., the first end 332, of the deflectable member 330 returns to its original position. As shown in FIGS. 20-21, the first end 332 of the deflectable member 330 may be visible through the viewing window 304 to indicate to a user the volume of contents within the container 306.

Figure 22:
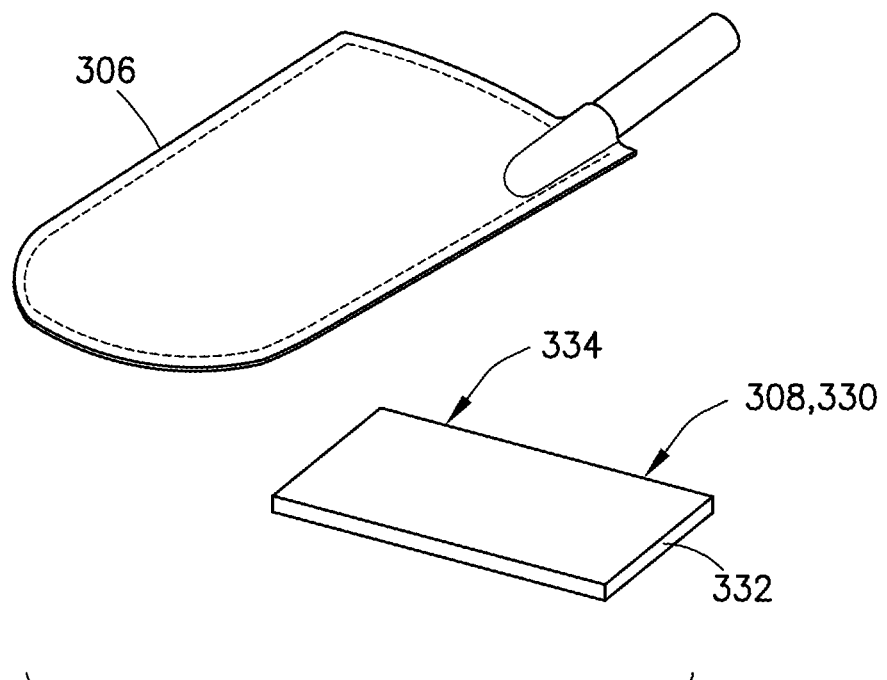
FIG. 22 is an exploded perspective view of a medicament container and a deflectable member in accordance with an embodiment of the present invention.
Figure 23:
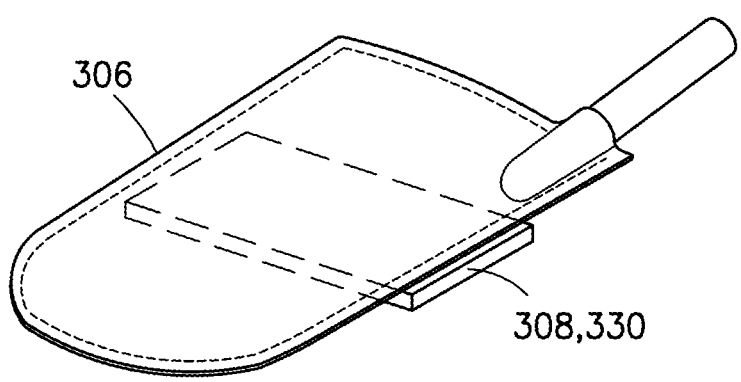
FIG. 23 is an assembled perspective view of a medicament container and a deflectable member in accordance with an embodiment of the present invention.

Referring to FIGS. 22 and 23, in one embodiment, the deflectable member 330 may be secured to the container 306, such as at one end of the deflectable member 330, via an adhesive 334. In other embodiments, similar fastening mechanisms may be used to secure the deflectable member 330 to the container 306.

In other configurations, it is anticipated herein that the visual identifier may be in the form of a viewable pattern. Optionally, a magnifying lens may be provided over the visual identifier and/or the visualizing window to provide for enhanced viewability of the visual identifier.

Figure 12:
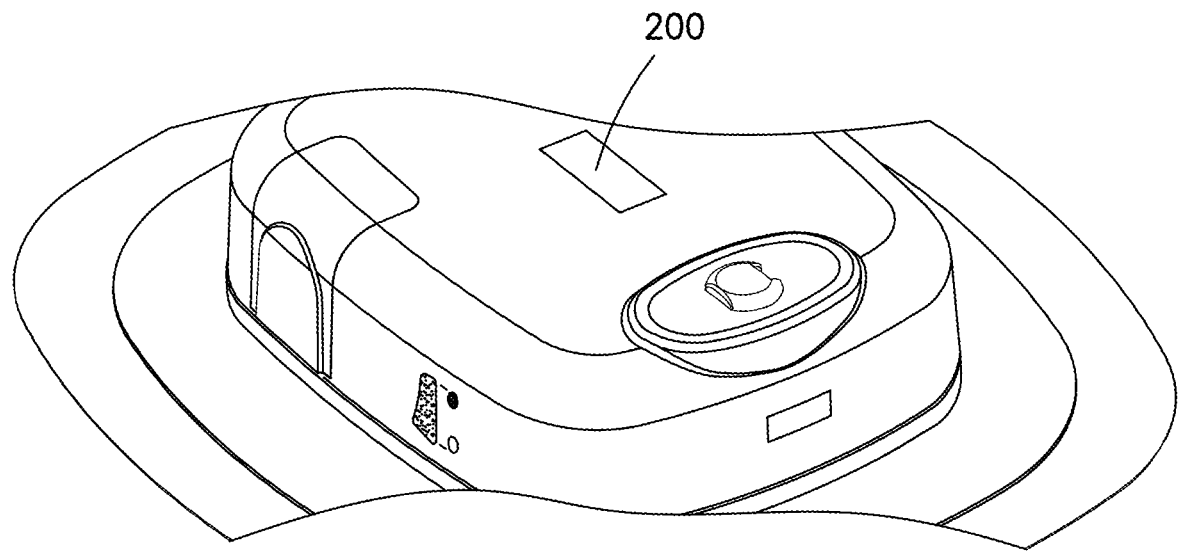

With reference to FIGS. 2-3, the delivery device 20 may also have at least one indicator 90. The at least one indicator 90 may be a visual indicator, an audible indicator, a tactile indicator, or a combination thereof. For example, the at least one indicator 90 may be a speaker, such as, without limitation, a piezo-buzzer, and/or a light, such as a light-emitting diode (LED) light. The LED may be a multi-color LED. In some examples, a plurality of LEDs of same or different colors may be provided. With reference to FIG. 12, the LED may be provided on a top surface of the delivery device 20 for easy viewing by the patient. The LED may be configured to walk-through certain drug delivery steps and/or error messaging for the benefit of the patient by altering the color of the LED, the rapidity at which the LED flashes, or through a transition of flashing and constant LED signals. The LED may be configured to indicate errors with the device, such as improper attachment to the patient, occlusions in the drug expulsion mechanism, low battery warnings, and the like. The LED may also be configured to indicate to the patient an end-of-dose indicator. Optionally, multiple indicators 90, such as multiple LEDs may be provided on opposing sides of the delivery device 20 to optimize viewing from multiple directions.

In other examples, the at least one indicator 90 is a display screen. The at least one indicator 90 may provide information about a status of the delivery device 20, such as, without limitation, when the delivery device 20 is delivering the pharmaceutical composition to the patient, when the delivery of the pharmaceutical agent is completed, and/or whether the delivery device 20 is paired with the notification device 30. Various other information about the status of the delivery device 20 may be provided by the at least one indicator 90. The at least one indicator 90 may be powered by a power source (not shown), such as a battery.

In other configurations, it is anticipated herein that an LED may also be provided in viewing window 200 to impart enhanced viewing of the visual indicator and/or to provide a status of the delivery device 20 itself.

The delivery device 20 may have one or more user input devices 100, such as one or more buttons. The one or more user input devices 100 can be used for configuring the delivery device 20, such as, without limitation, wirelessly connecting the delivery device 20 with the notification device 30 and/or activating the delivery device 20. In certain configurations, the delivery device 20 may include one or more input devices 100, such as one or more buttons that are translucent or at least partially translucent such that an indicator 90, such as an LED is viewable through the translucent or partially translucent buttons.

Figure 9:
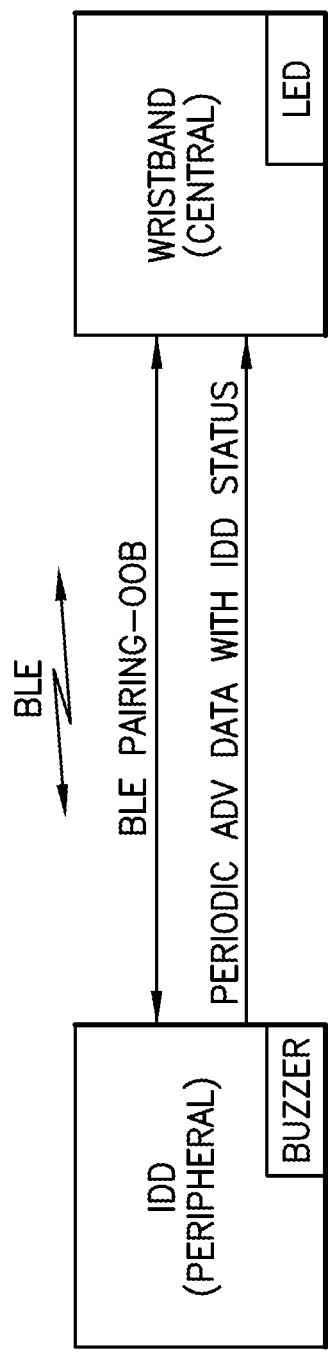
FIG. 9 is a schematic representation of a communication link between a wearable automatic injector and a notification device in accordance with an embodiment of the present invention.

The delivery device 20 has wireless communication circuitry 110, such as, without limitation, a Wi-Fi module, a Bluetooth™ module, a near field communication (NFC) module, or other wireless communication circuitry, such depicted with reference to FIG. 9. The wireless communication circuitry 110 is configured to allow the delivery device 20 to communicate with one or more other electronic devices, such as the notification device 30 or other device through a wireless connection. The wireless connection may be any Wi-Fi connection, Bluetooth™ connection, NFC connection, or other wireless connection. The wireless communication circuitry 110 may be configured for automatically pairing with one or more other electronic devices within the range of a wireless signal sent by the delivery device 20.

In some examples, the wireless communication circuitry 110 is configured to provide one-way communication with one or more other electronic devices, such as the notification device 30 or other device. The one-way communication with one or more electronic devices may include communicating information regarding at least one property of the delivery device 20, such as, without limitation, the delivery status of the delivery device 20, fill volume of the delivery device 20, whether the delivery device 20 is paired with one or more other electronic devices, and/or the type of pharmaceutical composition being delivered to the patient.

In other examples, the wireless communication circuitry 110 is configured to provide two-way communication with one or more other electronic devices, such as the notification device 30 or other device. The two-way communication with one or more electronic devices may include, without limitation, communicating information regarding at least one property of the delivery device 20, such as, without limitation, the delivery status of the delivery device 20, fill volume of the delivery device 20, whether the delivery device 20 is paired with one or more other electronic devices, and/or the type of pharmaceutical composition being delivered to the patient, and receiving information from the one or more electronic devices. In some examples, receiving information from one or more electronic devices may include control signals for controlling at least one aspect of the delivery device 20, such as the delivery status of the delivery device 20.

Notification Device

With reference to FIG. 4, one exemplary and non-limiting embodiment of the notification device 30 is shown. In the examples shown in FIG. 4, the notification device 30 is embodied as a wristband having a strap portion 120 and a display portion 130. The strap portion 120 is configured for being secured around a user's wrist W. In other examples, the notification device 30 may be a keychain, a pendant, a patch, a ring, a necklace, or any other wearable or non-wearable device configured for wirelessly communicating with the delivery device 20 to communicate information regarding at least one property of the delivery device 20, such as, without limitation, the delivery status of the delivery device 20, fill volume of the delivery device 20, whether the delivery device 20 is paired with the notification device 30, and/or the type of pharmaceutical composition being delivered to the patient.

With reference to FIGS. 5A-5D, the display portion 130 of the notification device 30 has at least one indicator 140. The at least one indicator 140 may be a visual indicator, an audible indicator, a tactile indicator, or a combination thereof. For example, the at least one indicator 140 may be a speaker, such as, without limitation, a piezo-buzzer, and/or a light, such as a light-emitting diode (LED) light. The LED may be a multi-color LED. In some examples, a plurality of LEDs of same or different colors may be provided. For example, in FIG. 5A, the notification device 30 is shown in a pre-use initial configuration. In FIG. 5B, the notification device 30 is activated and a first LED is visible and illuminated and extends about a first portion of the display indicating a first period of activation of the delivery device 20, such as delivery of a first pre-determined amount of medicament. In FIG. 5C, a second LED is visible and illuminated and extends about a second portion of the display indicating a second portion of activation of the delivery device 20, such as delivery of a second pre-determined amount of medicament. In FIG. 5D, a third LED is visible and illuminated and extends about a third portion of the display indicating a third portion of activation of the delivery device 20, such as delivery of a third pre-determined amount of medicament.

In other examples, the at least one indicator 140 is a display screen. The at least one indicator 140 may provide information about a status of the delivery device 20 and/or the notification device 30, such as, without limitation, when the delivery device 20 is delivering the pharmaceutical composition to the patient, when the delivery of the pharmaceutical agent is completed, whether the delivery device 20 is paired with the notification device 30, and/or the type of pharmaceutical composition being delivered to the patient. Various other information about the status of the delivery device 20 and/or the notification device 30 may be provided by the at least one indicator 140. The at least one indicator 140 may be powered by a power source (not shown), such as a battery.

The notification device 30 may have one or more user input devices 150, such as one or more buttons. The one or more user input devices 150 can be used for configuring the notification device 30, such as, without limitation, wirelessly connecting the notification device 30 with the delivery device 20 and/or activating the notification device 30.

The notification device 30 has wireless communication circuitry 160, such as a Wi-Fi module, a Bluetooth™ module, a near field communication (NFC) module, or other wireless communication circuitry. The wireless communication circuitry 160 is configured to allow the notification device 30 to communicate with one or more other electronic devices, such as the delivery device 20 or other device through a wireless connection. The wireless connection may be any Wi-Fi connection, Bluetooth™ connection, NFC connection, or other wireless connection. The wireless communication circuitry 160 may be configured for automatically pairing with one or more other electronic devices within the range of a wireless signal sent by the notification device 30.

In some examples, the wireless communication circuitry 160 is configured to provide one-way communication with one or more other electronic devices, such as the delivery device 20 or other device. The one-way communication with one or more electronic devices may include receiving information regarding at least one property of the delivery device 20, such as, without limitation, the delivery status of the delivery device 20, fill volume of the delivery device 20, whether the notification device 30 is paired with the delivery device 20, etc. In other examples, the wireless communication circuitry 160 is configured to provide two-way communication with one or more other electronic devices, such as the delivery device 20 or other device. The two-way communication with one or more electronic devices may include receiving information regarding at least one property of the delivery device 20 and sending information to the delivery device 20. In some examples, sending information to the delivery device 20 may include sending control signals for controlling at least one aspect of the delivery device 20, such as the delivery status of the delivery device 20.

In one or more examples, the notification device 30 may be connected to another electronic device (e.g., phone, laptop, tablet, etc.) through a wireless connection in order to control the notification device 30 and/or send status information about the notification device 30 and/or the delivery device 20.

In some examples, the notification device 30 may be mechanically and/or electrically connected with the delivery device 20 by a wired connection.

Method of Using the Administration System

Having described the structure of the administration system 10, a method of using the administration system 10 to deliver a dose of pharmaceutical composition to the patient will now be described with reference to FIGS. 6A-9.

Setup

A patient or the medical practitioner removes the delivery device 20 from packaging 170. In some examples, removal of the delivery device 20 from the packaging may automatically activate the delivery device 20 to a ready state. In other examples, the delivery device 20 may be activated after removal from packaging by pressing one or more user input devices 100, 150. In some examples, the patient or the medical practitioner may set a target dose of the pharmaceutical composition to be delivered to the patient.

The delivery device 20 and the notification device 30 are initially in an "off" state. The patient or the medical practitioner activates the delivery device 20 and the notification device 30 by actuating the one or more user input devices 100, 150, respectively, such as by pressing one or more buttons for a predetermined amount of time, such as approximately 1 second. The at least one indicator 90 on the delivery device 20 may indicate that the delivery device 20 has been turned on. For example, the LED light on the delivery device 20 may flash yellow at a predetermined interval such as, every 1 second, and the speaker may play an activation tone. Similarly, at least one indicator 140 on the notification device 30 may indicate that the notification device 30 has been turned on. For example, the LED light on the notification device 30 may flash green at a predetermined interval such as, every 0.5 seconds, and the speaker may play an activation tone.

Pairing

Upon activation, the delivery device 20 and the notification device 30 may activate the respective wireless communication circuitry 110, 160 to automatically pair the delivery device 20 to the notification device 30. The wireless communication circuitry 110, 160 may be active for a predetermined length of time, such as approximately 75 seconds, during which the notification device 30 that is within the range of the delivery device 20 will be paired with the delivery device 20. In some examples, the notification device 30 may use an out-of-band (OOB) method of pairing. When paired, the at least one indicator 90 on the delivery device 20 and the at least one indicator 140 on the notification device 30 may indicate a successful pairing of the notification device 30 with the delivery device 20. For example, the LED on the delivery device 20 may be turned off, while the LED light on the notification device 30 may flash green at a predetermined interval such as, every 0.5 seconds. If the notification device 30 and the delivery device 20 are not paired within the predetermined period, the notification device 30 and the delivery device 20 go into a standby mode.

Filling and Priming

The delivery device 20 may be filled and primed with the pharmaceutical composition. Once a desired dose of the pharmaceutical composition is filled and the delivery device 20 is primed, the at least one indicator 90 on the delivery device 20 and the at least one indicator 140 on the notification device 30 may indicate that the delivery device 20 is ready for use. In certain embodiments, and with specific reference to FIGS. 10A-10C, the container of the pharmaceutical composition 306 may be a reservoir bag which is at least partially visible through a viewing window 280 disposed in at least a portion of the housing of the delivery device 20. For example, the container 306 may be made from a flexible material which expands in size as a fluid medicament is filled into the container 306. Optionally, the container 306 may have a visual indicator integrally formed therewith. In one embodiment, the container 306 may be made of a material having a visually distinct color, such as a fluorescent green material, such that the positioning of the container 306 within the viewing window 280 is readily identifiable. In other configurations, a visual identifier may be stamped or painted onto at least a portion of the container 306. The visual identifier may be in the form of a line or other distinct patterning, or alternatively, the entire container 306 may include the visual identifier, such as an overall color of the container 306. Depending on the particular nature of the medicament to be provided into the container 306, it may be desirable to provide a container 306 that is light-impermeable.

As shown specifically in FIGS. 10A-10C, the delivery device 20 may have a fill-indicator display 270 which includes a fill-line display indicating the prior to filling/empty condition, the partially filled/delivered condition, and the filled condition of the container 306 disposed within the delivery device 20. In this configuration, the positioning of the reservoir bag 290 within the viewing window 280 can coincide with at least one indicator of the fill-indicator display 270 to indicate a state of fill of the device during both filling and delivery of a medicament. As the container 306 includes a readily-identifiable visual indicator, such as a horizontal line, a position of the container, such as a reservoir bag, can align with an indicator of the fill-indicator display 270 to communicate to a user the amount of medicament disposed within the container 306 during the filling or emptying process.

As shown in the first step of FIG. 10A, in the prior to filling (or fully emptied) condition, the visual identifier of the container 306 is aligned with the "empty" indicator of the fill-indicator display 270, conveying to the user that there is no appreciable medicament within the container 306. As shown in the second step of FIG. 10B, in the partially filled (or partially delivered) condition, the visual identifier of the container 306 is aligned with the intermediate indicator of the fill-indicator display 270, conveying to the user that there is an identified amount of medicament within the container 306. As shown in the third step of FIG. 10C, in the filled condition, the visual identifier of the container 306, such as a reservoir bag, is aligned with the "full" indicator of the fill-indicator display 270, conveying to the user that the device has a full dose of medicament within the container 306. It will also be appreciated herein that if the entire container 306 functions as the visual identifier, such as in the case in which the container 306 has an overall contrasting color, then the positioning of the container 306 itself with respect to the individual indicators of the fill-indicator display 270 will convey the amount of medicament within the container 306 to the user.

In some examples, it may be desired that the delivery of the dose of pharmaceutical composition be delayed by a predetermined length of time, such as, for example, about 27 hours. In some examples, the fill volume of the pharmaceutical composition and the preset delay may be configurable. The at least one indicator 90 on the delivery device 20 and the at least one indicator 140 on the notification device 30 may indicate the beginning of the delay period. For example, the LED on the notification device 30 may flash green every second.

Figure 6A:
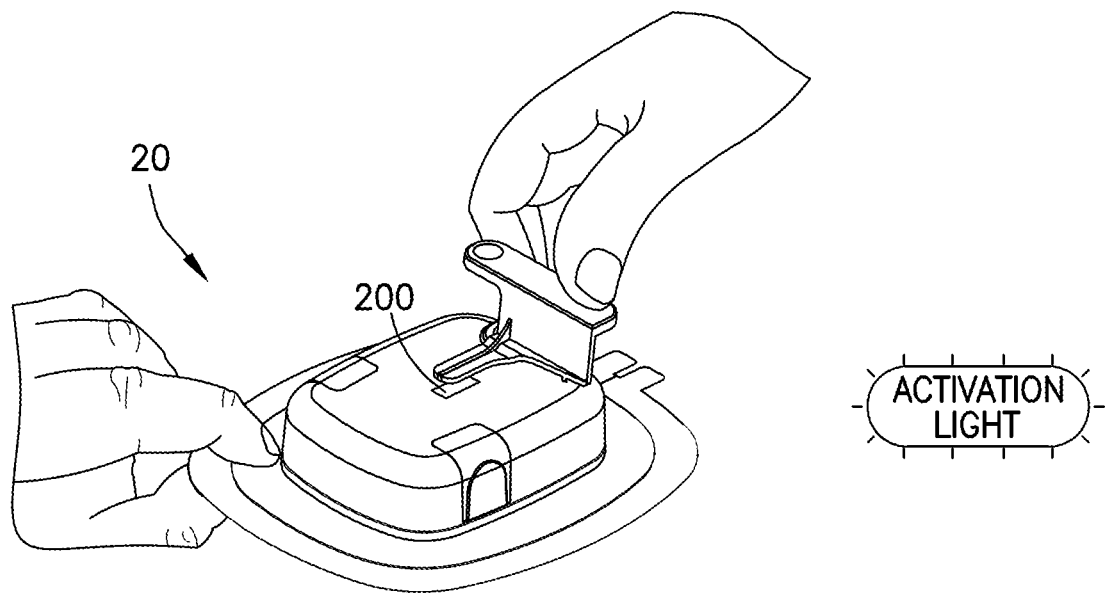
FIG. 6A is a perspective view of a user preparing the wearable automatic injector for attachment to a patient's skin in accordance with an embodiment of the present invention.
Figure 6B:
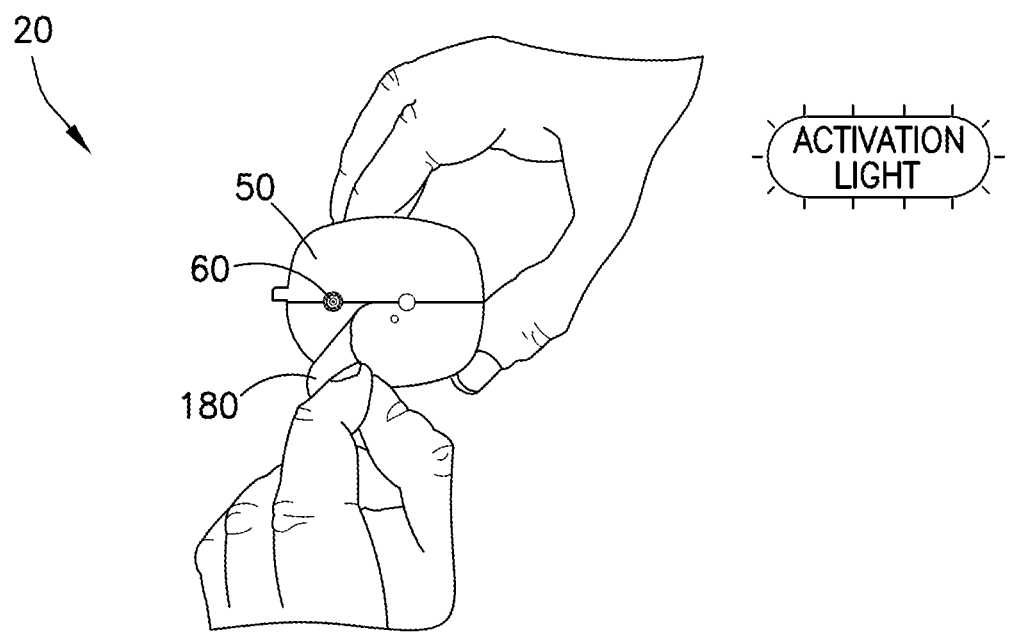
FIG. 6B is a perspective view of a user preparing the wearable automatic injector for attachment to a patient's skin in accordance with an embodiment of the present invention.
Figure 6C:
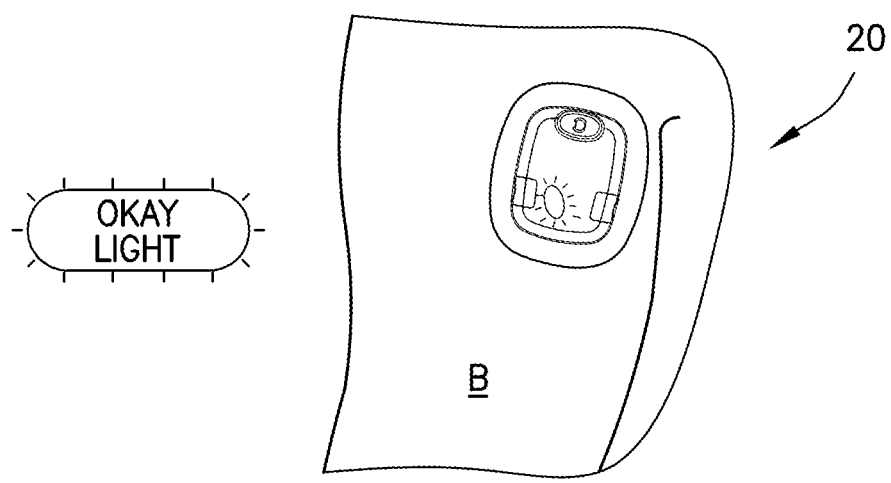
FIG. 6C is a top view of the wearable automatic injector as applied to the patient's skin and signaling activation of the device in accordance with an embodiment of the present invention.
Figure 6D:
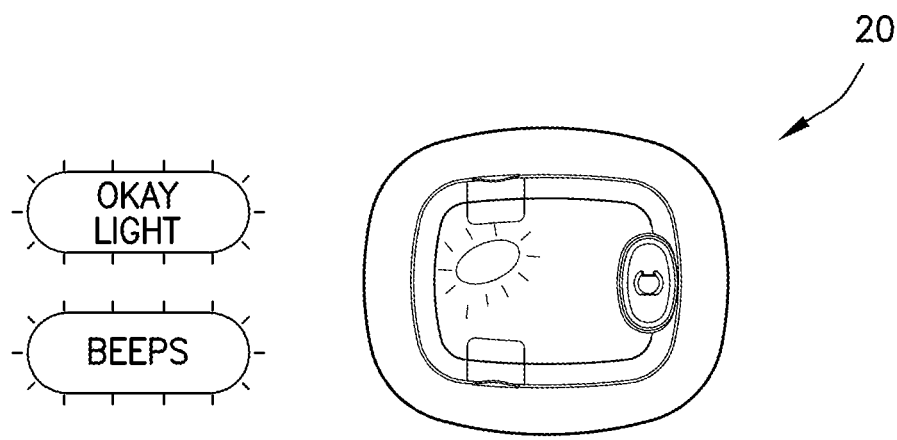
FIG. 6D is a top view of the wearable automatic injector in an activated state in accordance with an embodiment of the present invention.
Figure 7A:
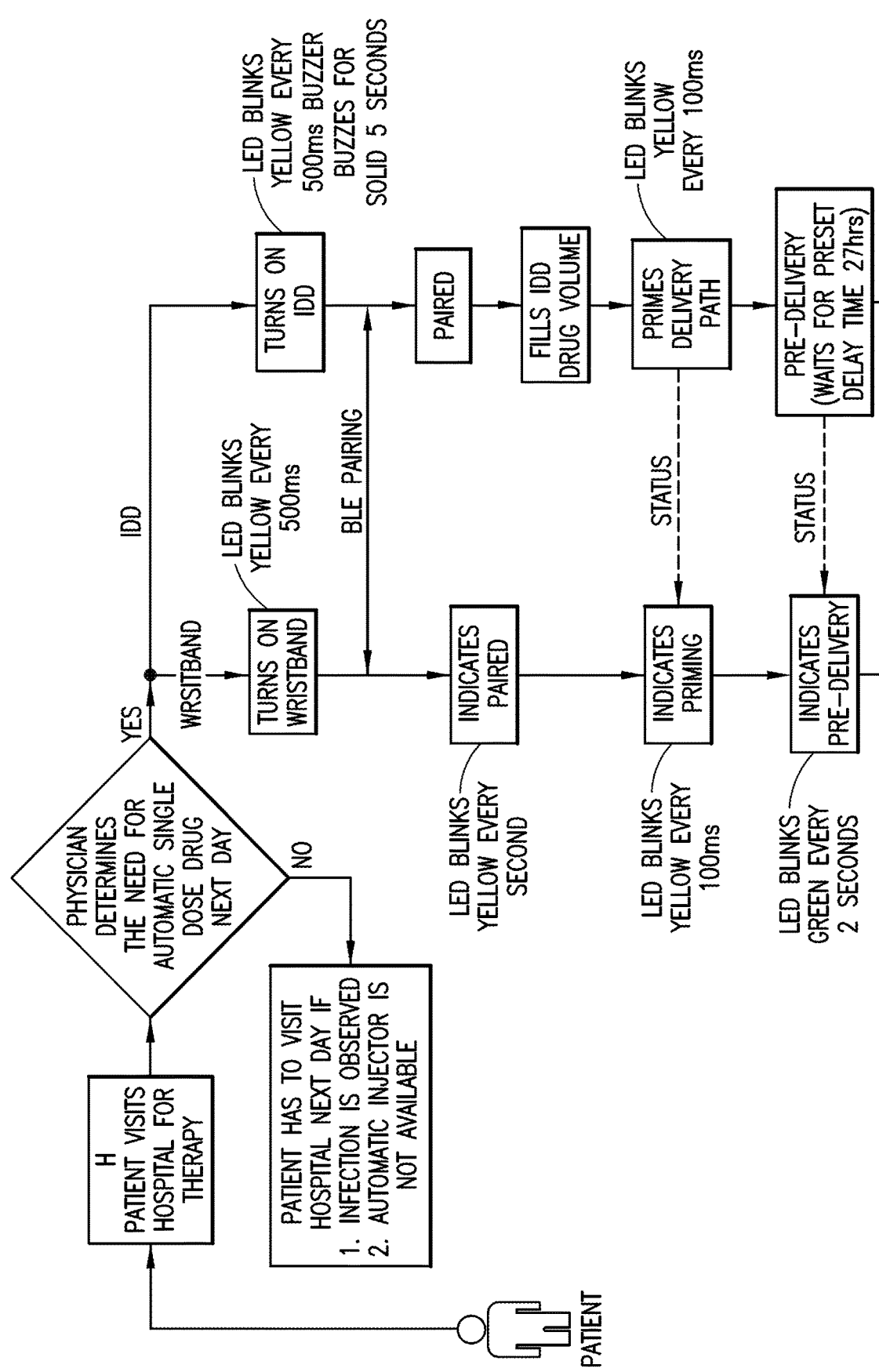
Figure 8A:
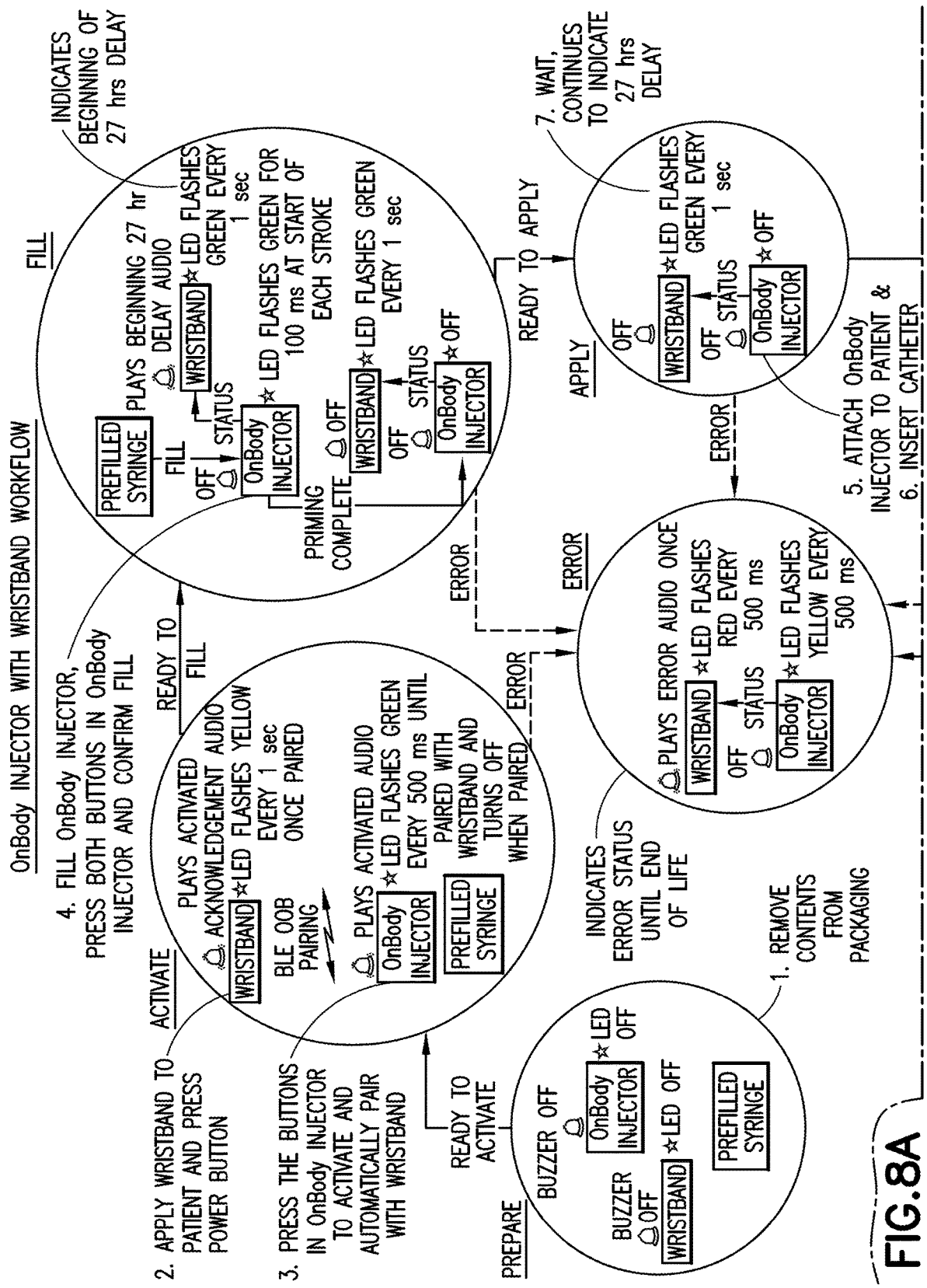
FIGS. 8A-8B are schematic representations of workflow for use of a wearable automatic injector and a notification device in accordance with an embodiment of the present invention.
Figure 8B:
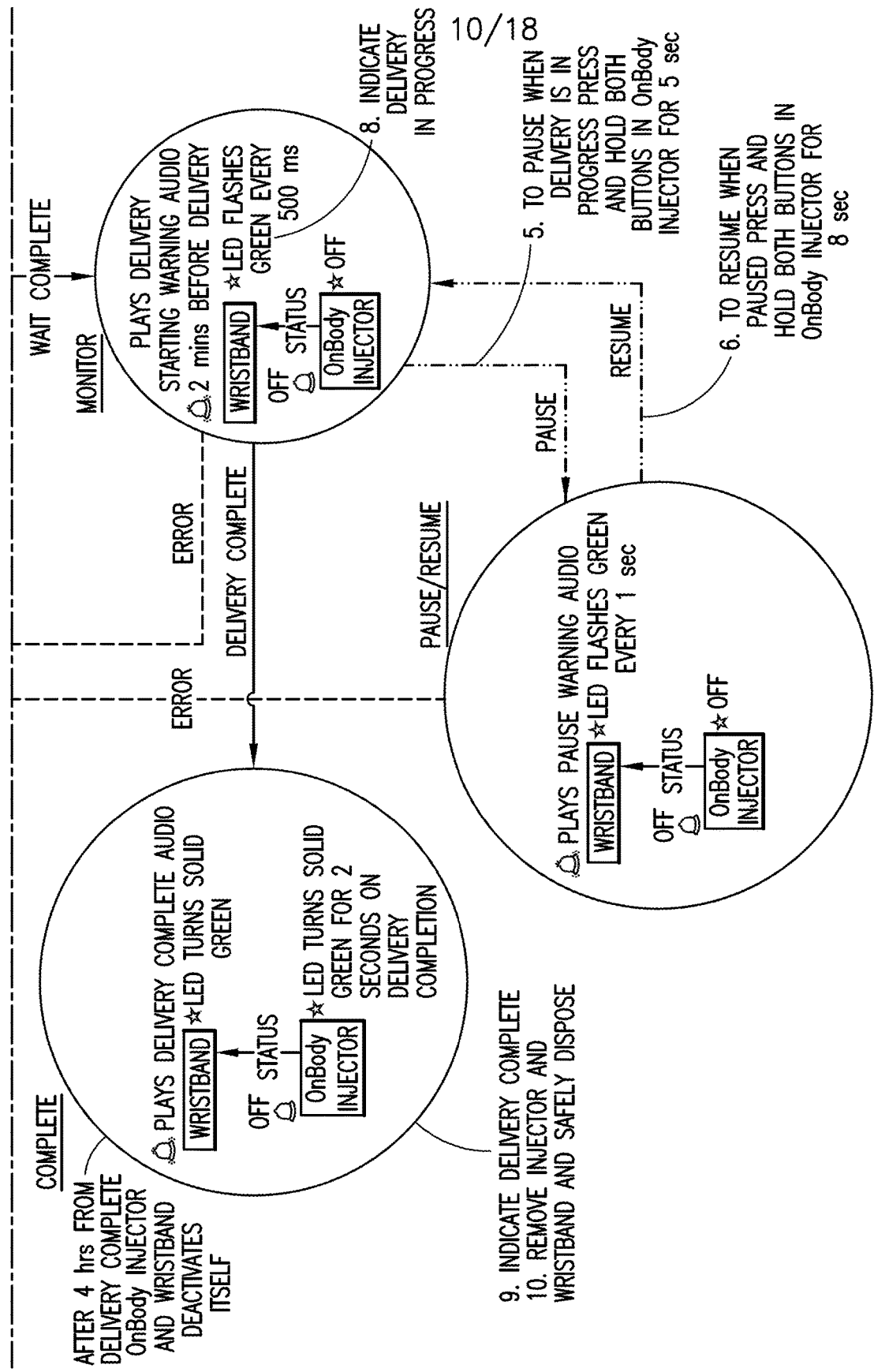

With reference to FIGS. 6B-6C, the filled and primed delivery device 20 is applied to the patient's body B by removing a protective covering 180 from the dermal pad 50 to expose the injection needle 60 and apply the dermal pad 50 to the patient's skin. The patient or the medical practitioner may activate the injection assembly to deploy the injection needle 60. The at least one indicator 90 on the delivery device 20 and the at least one indicator 140 on the notification device 30 may indicate when the injection needle 60 has been inserted into the patient's body.

Delivery

Upon priming and filling the delivery device 20 and attaching the delivery device 20 to the patient's body, the delivery device 20 will start the delivery of the pharmaceutical composition upon expiration of the delay period. Once the delivery process starts, the at least one indicator 90 on the delivery device 20 and the at least one indicator 140 on the notification device 30 may indicate that the delivery is in progress. For example, the LED on the notification device 30 may flash green every 0.5 seconds. The buzzer on the notification device 30 may indicate the start of the delivery procedure by producing a delivery tone. The delivery procedure may be paused when one or more of the user input devices 100 on the delivery device 20 are actuated. In some examples, the delivery procedure may be paused when one or more of the user input devices 150 on the notification device 30 are actuated. The delivery procedure may be resumed by actuating the one or more of the user input devices 100 on the delivery device 20, and/or one or more of the user input devices 150 on the notification device 30. The at least one indicator 90 on the delivery device 20 and the at least one indicator 140 on the notification device 30 may indicate that the delivery is completed. For example, the LED on the notification device 30 may be solid green. The delivery device 20 and the notification device 30 may automatically deactivate after the delivery is completed. When the delivery is completed, the delivery device 20 may be removed from the patient's body and discarded. The notification device 30 may be reusable with another delivery device 20, or it may be discarded after a single use.

In some examples, the at least one indicator 90 on the delivery device 20 and the at least one indicator 140 on the notification device 30 may be used to indicate an error message during administration of the pharmaceutical composition. In some examples, the LED on the delivery device 20 and/or the notification device 30 may flash red, and/or the speaker/buzzer on the delivery device 20 and/or the notification device 30 may sound a warning tone to instruct the patient to contact the medical practitioner.

In some examples, the notification device 30 may communicate, using wireless communication, the status of the notification device 30 and/or the delivery device 20 to a remote device, such as, without limitation, a computer, a laptop, or a smartphone (relay mode). In other examples, the notification device 30 may communicate, using wireless communication, the status of the notification device 30 and/or the delivery device 20 to the cloud (cell mode).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A delivery apparatus configured to deliver a dose of a medicament to a patient, the delivery apparatus comprising:
   a delivery device, comprising:
      a housing including a viewing window,
      a needle movable between a retracted position, in which the needle does not protrude outside the housing, and an extended position, in which the needle protrudes outside the housing,
      a flexible container disposed within the housing for storing the medicament therein, and
      a visual identifier aligned with a portion of the viewing window, wherein a position of the visual identifier relative to the viewing window is dependent on a volume of the medicament within the container; and
   a notification device in communication with the delivery device, the notification device configured to communicate information about a status of at least one property of the delivery device,
   wherein the delivery device is configured to move the needle between the retracted position and the extended position, and wherein the delivery device retracts the needle to the retracted position after the dose of the medicament to the patient is delivered,
   wherein the visual identifier is movable relative to the viewing window between an empty position, in which the container is empty, and a full position, in which the container is full, and
   wherein the visual identifier is disposed within the housing between the container and a deformable material.

2. The delivery apparatus of claim 1, wherein the visual identifier comprises a connector that is attachable to a portion of the container.

3. The delivery apparatus of claim 1, wherein as the container is filled with the medicament, the container expands and moves the visual identifier downward thereby compressing the deformable material.

4. The delivery apparatus of claim 1, wherein the deformable material comprises a foam.

5. The delivery apparatus of claim 1, wherein the visual identifier comprises a deflectable member.

6. The delivery apparatus of claim 1, wherein the housing comprises a fill-indicator display adjacent the viewing window.

7. The delivery apparatus of claim 1, wherein the container is a reservoir bag and the visual identifier is a portion of the reservoir bag.

8. The delivery apparatus of claim 1, wherein the viewing window is located in a sidewall of the housing.

9. The delivery apparatus of claim 1, wherein the delivery device is a wearable automatic injector removably attachable to a skin surface of the patient.

10. The delivery apparatus of claim 1, wherein the notification device is a wristband.

11. The delivery apparatus of claim 1, wherein the notification device is in passive one-way communication with the delivery device and wherein the notification device displays the status of the at least one property of the delivery device.

12. The delivery apparatus of claim 1, wherein the status of at least one property of the delivery device is at least one of a status of the flexible container, status of medication stored within the flexible container, an amount of medication within the flexible container, a status of whether the container is empty or full, or a status of whether the medicament has been expelled from the flexible container.

13. The delivery apparatus of claim 1, wherein the status of at least one property of the delivery device is at least one of when the delivery device is delivering the medicament to a patient, when the delivery of the medicament is complete, and whether the delivery device is paired with the notification device.

14. The delivery apparatus of claim 2, wherein the connector is attachable to a sealed edge of the container.

15. The delivery apparatus of claim 2, wherein the connector comprises an indicator clip.

16. The delivery apparatus of claim 3, wherein as the container delivers the medicament, the container shrinks and the deformable material expands thereby moving the visual identifier upward.

17. The delivery apparatus of claim 5, wherein as the container is filled with the medicament, the container expands and deflects one end of the deflectable member downward.

18. The delivery apparatus of claim 17, wherein as the container delivers the medicament, the container shrinks which allows the one end of the deflectable member to return to an original position.

19. The delivery apparatus of claim 6, wherein the visual identifier aligns with a portion of the fill-indicator display to identify an amount of the medicament within the container.

20. The delivery apparatus of claim 9, wherein the delivery device includes at least one indicator for communicating a condition of the delivery device to the patient.

21. A delivery apparatus configured to deliver a dose of a medicament to a patient, the delivery apparatus comprising:
   a delivery device, comprising:
      a housing including a viewing window,
      a needle movable between a retracted position, in which the needle does not protrude outside the housing, and an extended position, in which the needle protrudes outside the housing,
      a flexible container disposed within the housing for storing the medicament therein, and
      a visual identifier aligned with a portion of the viewing window, wherein a position of the visual identifier relative to the viewing window is dependent on a volume of the medicament within the container; and
   a notification device in communication with the delivery device, the notification device configured to communicate information about a status of at least one property of the delivery device, wherein the delivery device is configured to move the needle between the retracted position and the extended position, and wherein the delivery device retracts the needle to the retracted position after the dose of the medicament to the patient is delivered, wherein the visual identifier is movable relative to the viewing window between an empty position, in which the container is empty, and a full position, in which the container is at least partially full, and wherein as the container is filled with the medicament, the container expands and moves the visual identifier within the viewing window.

22. The delivery apparatus of claim 21, wherein as the container is filled with the medicament, the container expands and moves the visual identifier downward, deforming the deformable material.

23. The delivery apparatus of claim 21, wherein as the container delivers the medicament, the container shrinks and the deformable material expands thereby moving the visual identifier upward.

\* \* \* \* \*